United States Patent
Miklos et al.

(10) Patent No.: US 9,658,228 B2
(45) Date of Patent: May 23, 2017

(54) METHOD TO DETECT THE ONSET AND TO MONITOR THE RECURRENCE OF CHRONIC GRAFT VERSUS HOST DISEASE IN TRANSPLANTATION PATIENTS

(71) Applicant: THE BOARD OF TRUSTEES OF THE LELAND STANFORD JUNIOR UNIVERSITY, Palo Alto, CA (US)

(72) Inventors: David B. Miklos, Stanford, CA (US); Bita Sahaf, Palo Alto, CA (US); Leonore A. Herzenberg, Stanford, CA (US)

(73) Assignee: The Board of Trustees of the Leland University Junior University, Palo Alto, CA (US)

( * ) Notice: Subject to any disclaimer, the term of this patent is extended or adjusted under 35 U.S.C. 154(b) by 494 days.

(21) Appl. No.: 13/796,344

(22) Filed: Mar. 12, 2013

(65) Prior Publication Data
US 2014/0212378 A1    Jul. 31, 2014

Related U.S. Application Data

(60) Provisional application No. 61/758,650, filed on Jan. 30, 2013.

(51) Int. Cl.
*A61K 38/00* (2006.01)
*C12N 5/00* (2006.01)
*G01N 33/569* (2006.01)

(52) U.S. Cl.
CPC ............... *G01N 33/56972* (2013.01); *G01N 2333/70503* (2013.01); *G01N 2800/245* (2013.01)

(58) Field of Classification Search
None
See application file for complete search history.

(56) References Cited

PUBLICATIONS

Zorn et al., J Exp. Med. 2004, v.199, pp. 1133-1142.*
Socie G (2011) Chronic GVHD: a new risk score? Blood 117:6408-6409.
Socie G, et al. (2011) Chronic graft-versus-host disease: long-term results from a randomized trial on graftversus-host disease prophylaxis with or without anti-T-cell globulin ATG-Fresenius. Blood 117:6375-6382.
Kohrt He, et al. (2009) TLI and ATG conditioning with low risk of graft-versus-host disease retains antitumor reactions after allogeneic hematopoietic cell transplantation from related and unrelated donors. Blood 114:1099-1109.
Kuzmina Z, et al. (2011) Significant differences in B-cell subpopulations characterize patients with chronic graft-versus-host disease-associated dysgammaglobulinemia. Blood 117:2265-2274.
Sarantopoulos S, et al. (2007) High levels of B-cell activating factor in patients with active chronic graftversus-host disease. Clin Cancer Res 13:6107-6114.
Sarantopoulos S, et al. (2011) Recovery of B-cell homeostasis after rituximab in chronic graft-versus-host disease. Blood 117:2275-2283.
She K, et al. (2007) Altered Toll-like receptor 9 responses in circulating B cells at the onset of extensive chronic graft-versus-host disease. Biol Blood Marrow Transplant 13:386-397.
Sarantopoulos S, et al. (2009) Altered B-cell homeostasis and excess BAFF in human chronic graft-versushost disease. Blood 113:3865-74.
Miklos DB, et al. Antibody response to DBY minor histocompatibility antigen is induced after allogeneic stem cell transplantation and in healthy female donors. Blood 103:353-359.
Wechalekar A, Cranfield T, Sinclair D, and Ganzckowski M (2005) Occurrence of autoantibodies in chronic graft vs. host disease after allogeneic stem cell transplantation. Clin Lab Haematol 27:247-249.
Arai S, et al. (2012) Prophylactic rituximab after allogeneic transplantation decreases B-cell alloimmunity with low chronic GVHD incidence. Blood 119:6145-6154.
Allen JL, et al. (2012) B cells from patients with chronic GVHD are activated and primed for survival via BAFF-mediated pathways. Blood 120:2529-2536.
Schultz KR, et al. (2006) Toward biomarkers for chronic graft-versus-host disease: National Institutes of Health consensus development project on criteria for clinical trials in chronic graft-versus-host disease: III. Biomarker Working Group Report. Biol Blood Marrow Transplant 12:126-137.
Socie G (2011) Chronic GVHD: B cells come of age. Blood 117:2086-2087.
Deneberg S, Lerner R, Ljungman P, Ringden O, and Hagglund H (2007) Relapse of preB-All after rituximab treatment for chronic graft versus host disease: implications for its use? Med Oncol 24:354-356.
Kharfan-Dabaja, MA and Bazarbachi A (2010) Emerging role of CD20 blockade in allogeneic hematopoietic cell transplantation. Biol Blood Marrow Transplant 16:1347-1354.
Khartan-Dabaja MA, et al. (2009) Efficacy of rituximab in the setting of steroid-refractory chronic graftversus-host disease: a systematic review and meta-analysis. Biol Blood Marrow Transplant 15:1005-1013.
Zaja, F, et al. (2007) Treatment of refractory chronic GVHD with rituximab: a GITMO study. Bone Marrow Transplant 40:273-277.
Cutler C, et al. (2006) Rituximab for steroid-refractory chronic graft-versus-host disease. Blood 108:756262.
Miklos DB, et al. (2005) Antibody responses to H-Y minor histocompatibility antigens correlate with chronic graft-versus-host disease and disease remission. Blood 105:2973-2978.

(Continued)

*Primary Examiner* — Michail Belyavskyi
(74) *Attorney, Agent, or Firm* — McCarter & English LLP

(57) ABSTRACT

The described invention comprises a method for detecting the onset or monitoring the recurrence of chronic graft versus host disease (cGVHD) in a transplantation patient. The method comprises isolating peripheral blood mononuclear cells (PBMCs) from the transplantation patient and analyzing the isolated PBMCs to detect a biomarker specific for a donor cell. The detection of the biomarker is indicative of the onset or recurrence of cGVHD in the transplantation patient.

12 Claims, 7 Drawing Sheets

(56) References Cited

PUBLICATIONS

Yang Y, et al. (2012) Antigen-specific memory in B-1a and its relationship to natural immunity. Proc Nati Acad Sci U S A 109:5388-5393.
Yang Y, et al. (2012) Antigen-specific antibody responses in B-1a and their relationship to natural immunity. Proc Natl Acad Sci U S A 109:5382-5387.
Filipovich AH, et al. (2005) National Institutes of Health consensus development project on criteria for clinical trials in chronic graft-versus-host disease: I. Diagnosis and staging working group report. Biol Blood Marrow Transplant 11:945-956.
Millan MT, et al. (2002) Mixed chimerism and immunosuppressive drug withdrawal after HLA-mismatched kidney and hematopoietic progenitor transplantation. Transplantation 73:1386-1391.
Sahaf B, et al. (2008) Culturing of human peripheral blood cells reveals unsuspected lymphocyte responses relevant to HIV disease. Proc Natl Acad Sci U S A 105:5111-5116.
Young JS, et al (2012) Donor B cells in transplants augment clonal expansion and survival of pathogenic CD4+ T cells that mediate autoimmune-like chronic graft-versus-host disease. J Immunol 189:222-233.
Srinivasan M, et al. (2011) Donor B-cell alloantibody deposition and germinal center formation are required for the development of murine chronic GVHD and bronchiolitis obliterans. Blood 119:1570-1580.

\* cited by examiner

METHOD TO DETECT THE ONSET AND TO MONITOR THE RECURRENCE OF CHRONIC GRAFT VERSUS HOST DISEASE IN TRANSPLANTATION PATIENTS

STATEMENT OF GOVERNMENT FUNDING

This invention was made with government support under National Heart Lung and Blood Institute R21HL084318 and National Cancer Institute P01 CA049605. The government has certain rights in the invention.

CROSS-REFERENCE TO RELATED APPLICATIONS

This invention was made with Government support under contracts CA049605 and HL084318 awarded by the National Institutes of Health. The government has certain rights in this invention.

FIELD OF INVENTION

The described invention generally relates to a method for detecting the onset and monitoring the recurrence of chronic graft versus host disease in transplantation patients.

BACKGROUND OF THE INVENTION

Allogeneic hematopoietic cell transplantation (allo-HCT) is a potentially curative therapy for patients with leukemia or lymphoma. However, chronic graft versus host-disease (cGVHD) remains a significant cause of late morbidity and mortality (Socie G (2011) Chronic GVHD: a new risk score? Blood 117:6408-6409; Socie G, et al. (2011) Chronic graft-versus-host disease: long-term results from a randomized trial on graftversus-host disease prophylaxis with or without anti-T-cell globulin ATG-Fresenius. Blood 117:6375-6382; Kohrt H E, et al. (2009) TLI and ATG conditioning with low risk of graft-versus-host disease retains antitumor reactions after allogeneic hematopoietic cell transplantation from related and unrelated donors. Blood 114:1099-1109; Arai S, et al. (2012) Prophylactic rituximab after allogeneic transplantation decreases B-cell alloimmunity with low chronic GVHD incidence. Blood 119:6145-6154).

Several studies indicate that donor-derived alloreactive B and T cells are involved in pathogenesis of cGVHD. In support of a B cell role (Arai S, et al. (2012) Prophylactic rituximab after allogeneic transplantation decreases B-cell alloimmunity with low chronic GVHD incidence. Blood 119:6145-6154; Allen J L, et al. (2012) B cells from patients with chronic GVHD are activated and primed for survival via BAFF-mediated pathways. Blood 120:2529-2536; Kuzmina Z, et al. (2011) Significant differences in B-cell subpopulations characterize patients with chronic graft-versus-host disease-associated dysgammaglobulinemia. Blood 117:2265-2274; Sarantopoulos S, et al. (2007) High levels of B-cell activating factor in patients with active chronic graft-versus-host disease. Clin Cancer Res 13:6107-6114; Saran-topoulos S, et al. (2011) Recovery of B-cell homeostasis after rituximab in chronic graft-versus-host disease. Blood 117:2275-2283; She K, et al. (2007) Altered Toll-like receptor 9 responses in circulating B cells at the onset of extensive chronic graft-versus-host disease. Biol Blood Marrow Transplant 13:386-397), the presence of circulating autoantibody (Sarantopoulos S, et al. (2009) Altered B-cell homeostasis and excess BAFF in human chronic graft-versushost disease. Blood 113:3865-74) and alloantibody (Miklos D B, et al. Antibody response to DBY minor histocompatibility antigen is induced after allogeneic stem cell transplantation and in healthy female donors. Blood 103:353-359; Wechalekar A, Cranfield T, Sinclair D, and Ganzckowski M (2005) Occurrence of autoantibodies in chronic graft vs. host disease after allogeneic stem cell transplantation. Clin Lab Haematol 27:247-249) have been associated with development of cGVHD. Specifically, predominant B cell subsets have been demonstrated in patients with cGVHD and identified in different studies as naïve (Kuzmina Z, et al. (2011) Significant differences in B-cell subpopulations characterize patients with chronic graft-versus-host disease-associated dysgammaglobulinemia. Blood 117:2265-2274) and post germinal center B cells (Sarantopoulos S, et al. (2007) High levels of B-cell activating factor in patients with active chronic graftversus-host disease. Clin Cancer Res 13:6107-6114; Sarantopoulos S, et al. (2011) Recovery of B-cell homeostasis after rituximab in chronic graft-versus-host disease. Blood 117:2275-2283; Sarantopoulos S, et al. (2009) Altered B-cell homeostasis and excess BAFF in human chronic graft-versushost disease. Blood 113:3865-74). In addition, B cell related markers and antibodies have been recognized as biomarkers for characterization and scoring cGVHD (Schultz K R, et al. (2006) Toward biomarkers for chronic graft-versus-host disease: National Institutes of Health consensus development project on criteria for clinical trials in chronic graft-versus-host disease: III. Biomarker Working Group Report. Biol Blood Marrow Transplant 12:126-137; Socie G (2011) Chronic GVHD: B cells come of age. Blood 117:2086-2087). Finally, Rituximab, which depletes B cells, has been successfully used as cGVHD therapy (Sarantopoulos S, et al. (2011) Recovery of B-cell homeostasis after rituximab in chronic graft-versus-host disease. Blood 117:2275-2283; Deneberg S, Lerner R, Ljungman P, Ringden O, and Hagglund H (2007) Relapse of preB-ALL after rituximab treatment for chronic graft versus host disease: implications for its use? Med Oncol 24:354-356; Kharfan-Dabaja, M A and Bazarbachi A (2010) Emerging role of CD20 blockade in allogeneic hematopoietic cell transplantation. Biol Blood Marrow Transplant 16:1347-1354; Kharfan-Dabaja M A, et al. (2009) Efficacy of rituximab in the setting of steroid-refractory chronic graftversus-host disease: a systematic review and meta-analysis. Biol Blood Marrow Transplant 15:1005-1013; Zaja, F, et al. (2007) Treatment of refractory chronic GVHD with rituximab: a GITMO study. Bone Marrow Transplant 40:273-277; Cutler C, et al. (2006) Rituximab for steroid-refractory chronic graft-versus-host disease. Blood 108:756262).

Previous studies by our group have shown alloantibody responses occur in male HCT patients with female donors (F→M). These responses include donor derived alloreactive IgG that recognizes one or more Y chromosome encoded proteins (H-Y antigens), including the DDX3Y protein (referred to hereafter as DBY) and its immunodominant DBY-2 peptide, which we use in studies here. In addition, donor-derived anti-DBY antibodies appear in serum in association with cGVHD in F→M patients implicating alloreactive B cells in cGVHD pathogenesis (Miklos D B, et al. Antibody response to DBY minor histocompatibility antigen is induced after allogeneic stem cell transplantation and in healthy female donors. Blood 103:353-359; Miklos D B, et al. (2005) Antibody responses to H-Y minor histocompatibility antigens correlate with chronic graft-versus-host disease and disease remission. Blood 105:2973-2978). In order to test the hypothesis that H-Y specific B cells contribute to cGVHD pathogenesis, we have developed an H-Y specific FACS stain for their isolation and characterization.

Here, we demonstrate that 6 months after F→M transplant, more than half of 28 male patients with female donors develop circulating B cells whose surface IgM and IgG receptors specifically bind DBY-2, and hence are poised to undergo class switch and differentiate to plasma cells that produce IgG anti-DBY-2 antibodies. Further, we show that their presence in circulation is strongly associated with the development of cGVHD (p=0.004), that is, the overwhelming majority (15/16) of patients who have DBY-2 specific B cells either have or will develop cGVHD within 1-3 months. In contrast, only about half (5/12) of patients who do not have these B cells develop cGVHD. We detected immunoglobulin (Ig) M and IgG anti-DBY-2 B cells in all but 2 of the patients who later developed circulating IgG anti-DBY-2 (p=0.002).

As is usual in studies with antigen binding B cells in the mouse (Yang Y, et al. (2012) Antigen-specific memory in B-1a and its relationship to natural immunity. Proc Natl Acad Sci USA 109:5388-5393; Yang Y, et al. (2012) Antigen-specific antibody responses in B-1a and their relationship to natural immunity. Proc Natl Acad Sci USA 109: 5382-5387), the amount of the antigen bound to the B cells is strongly correlated with the amount of surface Ig on the cells, which at the time point we examined is exclusively IgM and IgD associated mainly with Igλ light chains. However, even though these cells have most likely arisen in response to antigenic stimulation (DBY-2 on the male patient's cells stimulating female donor B cells), they express a phenotype (CD19+IgM+IgD+CD38+ and CD27−) commonly taken as characteristic of transitional B cells that have recently entered circulation from bone marrow.

The prospective monitoring of anti-DBY-2 B cells may direct a more effective schedule for alloreactive B cell depletion therapy towards a goal of cGVHD prevention. Likewise, DBY-2 B cell monitoring may help elucidate whether current in vivo B cell depletion therapy for cGVHD effectively depletes these alloreactive B cells or if they persist and proliferate when cGVHD recurs.

SUMMARY OF THE INVENTION

B cells are known to play an important role in pathogenesis of human chronic graft-versus-host disease (cGVHD). Our group has previously shown that IgG allo-antibodies recognize Y chromosome encoded proteins (H-Y) and a dominant H-Y epitope (DBY-2) detectable 6-12 months after transplant in male patients who receive grafts from female donors (F→M HCT). Here we present fluorescence-activated cell sorting (FACS) studies of peripheral blood mononuclear cells (PBMC) collected 6 months post-transplant showing that 16/28 (57%) F→M HCT patients have circulating donor B cells that express B cell receptor (mainly IgM and Igλ) specific for DBY-2. The detection of these DBY-2 B cells 6 months after HCT are associated with chronic graft versus host disease (cGVHD) development (p=0.004). Specifically, 15 of 16 F→M with DBY-2 B cells developed cGVHD. In contrast, cGVHD developed in only 5 of the 12 who did not have DBY-2 B cells detected. This is the first demonstration of circulating human B cells binding an alloantigen (DBY-2) and the first demonstration that these DBY-2 specific B cells appear prior to development of cGVHD in roughly half of the F→M patients. Our study suggests that detection of anti DBY-2 B cells may predict cGVHD.

The present disclosure provides methods, compositions and kits useful to provide evidence of onset and to monitor recurrence of chronic graft versus host disease (cGVHD) in subjects who have received a hematopoietic cell transplantation allograft.

According to one aspect, the described invention provides a method for warning of onset of chronic graft versus host disease (cGvHD) prior to appearance of symptoms of cGvHD in a patient following a hematopoietic cell transplantation therapy with a hematopoietic cell allograft, comprising isolating peripheral blood mononuclear cells (PBMCs) from the patient at a time after the therapy; analyzing the isolated PBMCs, and specifically detecting a first biomarker expressed by circulating cells of the patient that reacts with a second biomarker expressed by genetically distinct cells, wherein the detecting of the cells that express the first biomarker indicates likely imminent onset of cGVHD in the patient; and initiating immune therapy to mitigate symptoms of cGvHD resulting from the transplant.

According to another aspect, the described invention provides a method for warning of recurrence of chronic graft versus host disease (cGvHD) prior to appearance of symptoms of cGvHD in a patient who, following hematopoietic cell transplantation therapy with a hematopoietic cell allograft, developed and was treated for cGvHD, which is in remission, comprising isolating peripheral blood mononuclear cells (PBMCs) from the patient at a time after the therapy; analyzing the isolated PBMCs, and specifically detecting a first biomarker expressed by circulating cells of the patient that reacts with a second biomarker expressed by genetically distinct cells, wherein the detecting of the cells that express the first biomarker indicates likely imminent onset of cGVHD in the patient; and initiating immune therapy to treat the recurrence of the cGvHD resulting from the transplant.

According to one embodiment, the circulating cells expressing the first biomarker are B lymphocytes with receptors that detect the first biomarker. According to another embodiment, the circulating cells are derived from the hematopoietic cell allograft.

According to one embodiment, the first biomarker is an antibody, the hematopoietic cell allograft contains cells that express the antibody, and the antibody reacts with the second biomarker expressed by the patient's cells.

According to one embodiment, the second biomarker is a Y-chromosome encoded H-Y antigen. According to another embodiment, the H-Y antigen is DBY-2.

According to one embodiment, the recipient patient is male, the recipient's cells express the second biomarker, and the second biomarker is the Y-chromosome encoded H—Y antigen, the donor is female, the donor's cells express the first biomarker, and the first biomarker is an antibody, which binds to the second biomarker, which is the H-Y antigen expressed by the patient's cells, wherein the recipient patient and donor are genetically distinct. According to another embodiment, the donor's cells that express the first biomarker are B lymphocytes. According to another embodiment, the phenotype of the B lymphocytes is CD19+.

According to one embodiment, the time after therapy for detecting the first biomarker expressed by circulating cells of the patient is within 1 year after transplantation. According to another embodiment, the time after therapy for detecting the first biomarker expressed by circulating cells of the patient is within 180 days after transplantation. According to another embodiment, the time after therapy for detecting the first biomarker expressed by circulating cells of the patient is within 155 days after transplantation. According to another embodiment, the time after therapy for detecting the first biomarker expressed by circulating cells of the patient is within 90 days after transplantation.

According to one embodiment, the detecting of the first biomarker expressed by circulating cells of the patient precedes development of circulating antibodies to a donor cell antigen in the patient.

According to one embodiment, the analyzing step is performed using flow cytometry.

BRIEF DESCRIPTION OF THE DRAWINGS

FIG. 2 depicts anti-DBY-2 B cell development, anti-DBY-2 Ig, and severity of cGVHD in 28 F→M HCT patients.

DETAILED DESCRIPTION OF THE INVENTION

Figure 1:
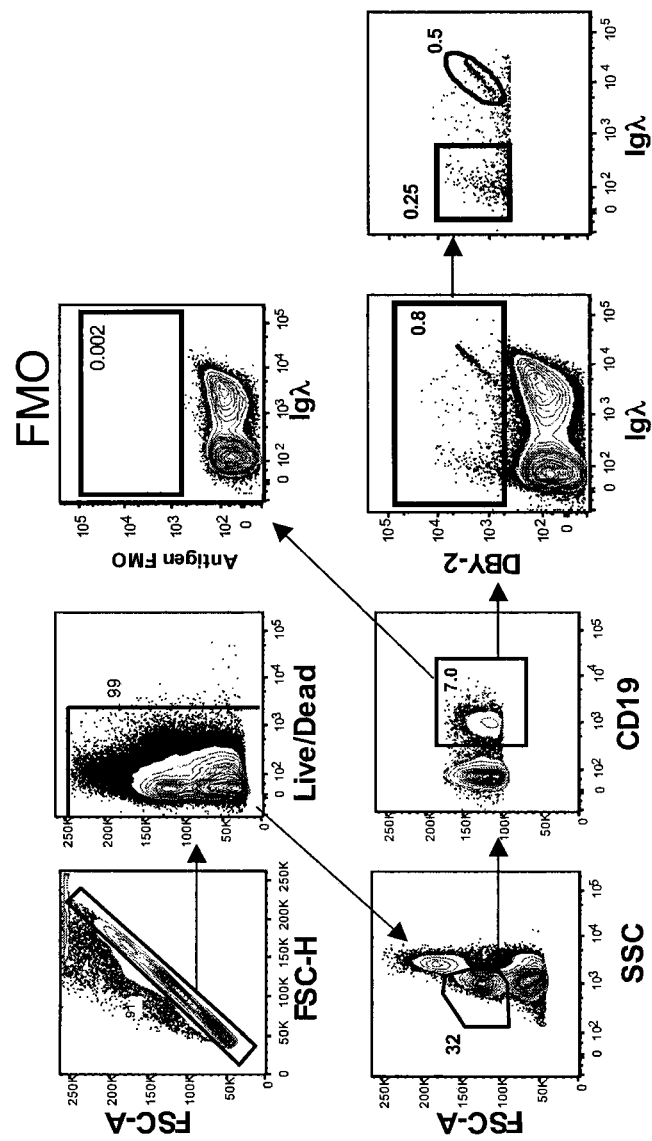
FIG. 1 depicts gated FACS data for a representative 6 month sample containing 0.8% DBY-2 binding B cells that are shown staining positive for CD19 and DBY-2. The Fluorescence Minus One (FMO) control gate excludes cells that non-specifically bound the fluoro-chrome coupled DBY-2 peptide (Y-axis) and define the DBY-2 binding threshold. DBY-2 binding B cells are shown to express Igκ or Igλ light chains 180 days following F→M HCT.

The described invention can be better understood from the following description of exemplary embodiments, taken in conjunction with the accompanying figures and drawings. It should be apparent to those skilled in the art that the described embodiments of the present invention provided herein are merely exemplary and illustrative and not limiting.

DEFINITIONS

Various terms used throughout this specification shall have the definitions set out herein.

The term "activation marker" as used herein, refers to an intracellular or cell surface marker that is highly associated with a particular cell and is selectively upregulated during a physiological condition. The physiological condition may be exposure to a substance, an allergen, a drug, a protein or a chemical, or other stimuli, or removal of a stimuli, a substance, a protein, an allergen, a drug or a chemical.

The term "antigen" and its various grammatical forms refers to any substance that can stimulate the production of antibodies and/or can combine specifically with them. The term "antigenic determinant" or "epitope" as used herein refers to an antigenic site on a molecule.

The term "autologous" as used herein, means derived from the same organism.

The term "allogeneic" as used herein, refers to being genetically different although belonging to or obtained from the same species.

Antibodies:

Antibodies are serum proteins the molecules of which possess small areas of their surface that are complementary to small chemical groupings on their targets. These complementary regions (referred to as the antibody combining sites or antigen binding sites) of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

Human antibodies show two kinds of light chains, κ and λ; individual molecules of immunoglobulin generally are only one or the other. In normal serum, 60% of the molecules have been found to have κ determinants and 30 percent λ. Many other species have been found to show two kinds of light chains, but their proportions vary. For example, in the mouse and rat, λ chains comprise but a few percent of the total; in the dog and cat, κ chains are very low; the horse does not appear to have any κ chain; rabbits may have 5 to 40% λ, depending on strain and b-locus allotype; and chicken light chains are more homologous to λ than κ.

In mammals, there are five classes of antibodies, IgA, IgD, IgE, IgG, and IgM, each with its own class of heavy chain—α a (for IgA), δ (for IgD), ε (for IgE), γ (for IgG) and μ (for IgM). In addition, there are four subclasses of IgG immunoglobulins (IgG1, IgG2, IgG3, IgG4) having γ1, γ2, γ3, and γ4 heavy chains respectively. In its secreted form, IgM is a pentamer composed of five four-chain units, giving it a total of 10 antigen binding sites. Each pentamer contains one copy of a J chain, which is covalently inserted between two adjacent tail regions.

All five immunoglobulin classes differ from other serum proteins in that they show a broad range of electrophoretic mobility and are not homogeneous. This heterogeneity—that individual IgG molecules, for example, differ from one another in net charge—is an intrinsic property of the immunoglobulins.

An antigenic determinant or epitope is an antigenic site on a molecule. Sequential antigenic determinants/epitopes essentially are linear chains. In ordered structures, such as helical polymers or proteins, the antigenic determinants/epitopes essentially would be limited regions or patches in or on the surface of the structure involving amino acid side chains from different portions of the molecule which could come close to one another. These are conformational determinants.

The principle of complementarity, which often is compared to the fitting of a key in a lock, involves relatively weak binding forces (hydrophobic and hydrogen bonds, van der Waals forces, and ionic interactions), which are able to act effectively only when the two reacting molecules can approach very closely to each other and indeed so closely that the projecting constituent atoms or groups of atoms of one molecule can fit into complementary depressions or recesses in the other. Antigen-antibody interactions show a high degree of specificity, which is manifest at many levels. Brought down to the molecular level, specificity means that the combining sites of antibodies to an antigen have a complementarity not at all similar to the antigenic determinants of an unrelated antigen. Whenever antigenic determinants of two different antigens have some structural similarity, some degree of fitting of one determinant into the combining site of some antibodies to the other may occur, and that this phenomenon gives rise to cross-reactions. Cross reactions are of major importance in understanding the complementarity or specificity of antigen-antibody reactions. Immunological specificity or complementarity makes possible the detection of small amounts of impurities/contaminations among antigens. The term "cross-reactivity" as used herein refers to situations in which antigenic determinants of two different antigens have some structural similarity, as a result of which some degree of fitting of one determinant into the combining site of some antibodies to the other may occur.

Monoclonal antibodies (mAbs) can be generated by fusing mouse spleen cells from an immunized donor with a mouse myeloma cell line to yield established mouse hybridoma clones that grow in selective media. A hybridoma cell is an immortalized hybrid cell resulting from the in vitro fusion of an antibody-secreting B cell with a myeloma cell. In vitro immunization, which refers to primary activation of antigen-specific B cells in culture, is another well-established means of producing mouse monoclonal antibodies.

Diverse libraries of immunoglobulin heavy (VH) and light (Vκ and Vλ) chain variable genes from peripheral blood lymphocytes also can be amplified by polymerase chain reaction (PCR) amplification. Genes encoding single polypeptide chains in which the heavy and light chain variable domains are linked by a polypeptide spacer (single chain Fv or scFv) can be made by randomly combining heavy and light chain V-genes using PCR. A combinatorial library then can be cloned for display on the surface of filamentous bacteriophage by fusion to a minor coat protein at the tip of the phage.

The technique of guided selection is based on human immunoglobulin V gene shuffling with rodent immunoglobulin V genes. The method entails (i) shuffling a repertoire of human λ light chains with the heavy chain variable region (VH) domain of a mouse monoclonal antibody reactive with an antigen of interest; (ii) selecting half-human Fabs on that antigen (iii) using the selected λ light chain genes as "docking domains" for a library of human heavy chains in a second shuffle to isolate clone Fab fragments having human light chain genes; (v) transfecting mouse myeloma cells by electroporation with mammalian cell expression vectors containing the genes; and (vi) expressing the V genes of the Fab reactive with the antigen as a complete IgG1, λ antibody molecule in the mouse myeloma.

The term "biomarkers" (or "biosignatures") as used herein, refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention.

The term "pre B lymphocyte" refers to an early B lymphoid type cell that is recognized by immunofluorescence as a μ positive, L chain negative bone marrow cell.

The term "B lymphocyte" or "B cell" refers to a short lived immunologically important lymphocyte that is not thymus dependent and is involved in humoral immunity. It expresses immunoglobulins on its surface but does not release them. A mature B lymphocyte can be activated by the binding of an antigen to cell surface receptors, which induces proliferation of the cell, resulting in a clone of cells specific for that antigen. With interaction with helper T lymphocytes, these cells then can differentiate to mature plasma cells, which secrete immunoglobulin molecules.

The term "cytokine" as used herein, refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The term "cell surface marker" as used herein, refers to an antigenic determinant or epitope found on the surface of a specific type of cell. Cell surface markers can facilitate the characterization of a cell type, its identification, and its isolation. Cell sorting techniques are based on cellular biomarkers where a cell surface marker(s) may be used for either positive selection or negative selection, i.e., for inclusion or exclusion, from a cell population.

Cluster of Differentiation

The cluster of differentiation (CD) system is a protocol used for the identification of cell surface molecules present on white blood cells. CD molecules can act in numerous ways, often acting as receptors or ligands; by which a signal cascade is initiated, altering the behavior of the cell. Some CD proteins do not play a role in cell signaling, but have other functions, such as cell adhesion. Generally, a proposed surface molecule is assigned a CD number once two specific monoclonal antibodies (mAb) are shown to bind to the molecule. If the molecule has not been well-characterized, or has only one mAb, the molecule usually is given the provisional indicator "w."

The CD system nomenclature commonly used to identify cell markers thus allows cells to be defined based on what molecules are present on their surface. These markers often are used to associate cells with certain immune functions. While using one CD molecule to define populations is uncommon, combining markers has allowed for cell types with very specific definitions within the immune system. There are more than 350 CD molecules identified for humans.

CD molecules are utilized in cell sorting using various methods, including flow cytometry. Cell populations usually are defined using a "+" or a "−" symbol to indicate whether a certain cell fraction expresses ("+") or lacks ("−") a CD molecule. For example, a "CD34+, CD31−" cell is one that expresses CD34, but not CD31. Table 1 shows commonly used markers employed by skilled artisans to identify and characterize differentiated white blood cell types:

| Type of Cell | CD Markers |
| --- | --- |
| Stem cells | CD34+, CD31− |
| All leukocyte groups | CD45+ |
| Granulocyte | CD45+, CD15+ |
| Monocyte | CD45+, CD14+ |
| T lymphocyte | CD45+, CD3+ |
| T helper cell | CD45+, CD3+, CD4+ |
| Cytotoxic T cell | CD45+, CD3+, CD8+ |
| B lymphocyte | CD45+, CD19+ or CD45+, CD20+ |
| Thrombocyte | CD45+, CD61+ |
| Natural killer cell | CD16+, CD56+, CD3− |

CD molecules used in defining leukocytes are not exclusively markers on the cell surface. Most CD molecules have an important function, although only a small portion of known CD molecules have been characterized. For example, there are over 350 CD for humans identified thus far.

CD3 (TCR complex) is a protein complex composed of four distinct chains. In mammals, the complex contains a CD3γ chain, a CD3δ chain, and two CD3ε chains, which associate with the T cell receptor (TCR) and the ζ-chain to generate an activation signal in T lymphocytes. Together, the TCR, the ζ-chain and CD3 molecules comprise the TCR complex. The intracellular tails of CD3 molecules contain a conserved motiff known as the immunoreceptor tyrosine-based activation motif (ITAM), which is essential for the signaling capacity of the TCR. Upon phosphorylation of the ITAM, the CD3 chain can bind ZAP70 (zeta associated protein), a kinase involved in the signaling cascade of the T cell.

CD14 is a cell surface protein expressed mainly by macrophages and, to a lesser extent, neutrophil granulocytes. CD14+ cells are monocytes that can differentiate into a host of different cells; for example, differentiation to dendritic cells is promoted by cytokines such as GM-CSF and IL-4. CD14 acts as a co-receptor (along with toll-like receptor (TLR) 4 and lymphocyte antigen 96 (MD-2)) for the detection of bacterial lipopolysaccharide (LPS). CD14 only can bind LPS in the presence of lipopolysaccharide binding protein (LBP).

CD15 (3-fucosyl-N-acetyl-lactosamine; stage specific embryonic antigen 1 (SSEA-1)) is a carbohydrate adhesion molecule that can be expressed on glycoproteins, glycolipids and proteoglycans. CD15 commonly is found on neutrophils and mediates phagocytosis and chemotaxis.

CD16 is an Fc receptor (FcγRIIIa and FcγRIIIb) found on the surface of natural killer cells, neutrophil polymorphonuclear leukocytes, monocytes and macrophages. Fc receptors bind to the Fc portion of IgG antibodies.

CD19 is a human protein expressed on follicular dendritic cells and B cells. This cell surface molecule assembles with the antigen receptor of B lymphocytes in order to decrease the threshold for antigen receptor-dependent stimulation. It generally is believed that, upon activation, the cytoplasmic tail of CD19 becomes phosphorylated, which allows binding by Src-family kinases and recruitment of phosphoinositide 3 (PI-3) kinases (See, https://www.beckmancoulter.com/wsrportal/wsrportal.portal?_nfpb=true&_windowLabel=UCM_RENDERER&_urlType=render&wlpUCM_RENDERER_path=%2Fwsr%2Fresearch-and-discovery%2Fproducts-and-services %2Fflow-cytometry%2Fb-cells%2Findex.htm).

CD20 is a non-glycosylated phosphoprotein expressed on the surface of all mature B-cells. Studies suggest that CD20 plays a role in the development and differentiation of B-cells into plasma cells. CD20 is encoded by a member of the membrane-spanning 4A gene family (MS4A). Members of this protein family are characterized by common structural features and display unique expression patterns among hematopoietic cells and nonlymphoid tissues.

CD27 normally is found on most peripheral blood T lymphocytes, medullary thymocytes and a subpopulation of circulating B lymphocytes. CD27 is a member of the TNF-receptor superfamily. This receptor is required for the generation and maintenance of T cell immunity. CD27 binds CD70 and plays a key role in regulating B cell activation and immunoglobulin synthesis. CD27 transduces signals that lead to the activation of NF-kappaB and MAPK8/JNK (See, http://www.ncbi.nlm.nih.gov/gene/939 and http://www.bd-biosciences.com/ptProductjsp?prodId=22387).

CD31 (platelet/endothelial cell adhesion molecule; PECAM1) normally is found on endothelial cells, platelets, macrophages and Kupffer cells, granulocytes, T cells, natural killer cells, lymphocytes, megakaryocytes, osteoclasts and neutrophils. CD31 has a key role in tissue regeneration and in safely removing neutrophils from the body. Upon contact, the CD31 molecules of macrophages and neutrophils are used to communicate the health status of the neutrophil to the macrophage.

CD34 is a monomeric cell surface glycoprotein normally found on hematopoietic cells, endothelial progenitor cells, endothelial cells of blood vessels, and mast cells. The CD34 protein is a member of a family of single-pass transmembrane sialomucin proteins and functions as a cell-cell adhesion factor. Studies suggest that CD34 also may mediate the attachment of stem cells to bone marrow extracellular matrix or directly to stromal cells.

CD38 is a multifunctional ectoenzyme expressed on hematopoietic cells, B cells, T cells, Natural Killer cells, monocytes and macrophages. CD38 functions in cell adhesion, signal transduction and calcium signaling (See, http://www.ncbi.nlm.nih.gov/gene/952).

CD45 (protein tyrosine phosphatase, receptor type, C; PTPRC) cell surface molecule is expressed specifically in hematopoietic cells. CD45 is a protein tyrosine phosphatase (PTP) with an extracellular domain, a single transmembrane segment, and two tandem intracytoplasmic catalytic domains, and thus belongs to receptor type PTP. Studies suggest it is an essential regulator of T-cell and B-cell antigen receptor signaling that functions by direct interaction with components of the antigen receptor complexes, or by activating various Src family kinases required for antigent receptor signaling. CD45 also suppresses JAK kinases, and thus functions as a regulator of cytokine receptor signaling. The CD45 family consists of multiple members that are all products of a single complex gene. Various known isoforms of CD45 include: CD45RA, CD45RB, CD45RC, CD45RAB, CD45RAC, CD45RBC, CD45RO, and CD45R (ABC). Different isoforms may be found on different cells. For example, CD45RA is found on naïve T cells and CD45RO is found on memory T cells (See, https://www.beckmancoulter.com/wsrportal/wsrportal.portal?_nfpb=true&_windowLabel=UCM_RENDERER&_urlType=render&wlpUCM_RENDERER_path=%2Fwsr%2Fresearch-and-discovery%2Fproducts-and-services%2Fflow-cytometry%2Fb-cells%2Findex.htm).

CD56 (neural cell adhesion molecule, NCAM) is a homophilic binding glycoprotein expressed on the surface of neurons, glia, skeletal muscle and natural killer cells. It generally is believed that NCAM has a role in cell-cell adhesion, neurite outgrowth, and synaptic plasticity. There are three known main isoforms of NCAM, each varying only in their cytoplasmic domains: NCAM-120 kDa (glycosylphopharidylinositol (GPI) anchored); NCAM-140 kDa (short cytoplasmic domain); and NCAM (long cytoplasmic domain). The different domains of NCAM have different roles, with the Ig domains being involved in homophilic binding to NCAM, and the fibronection type III (FNIII) domains being involved in signaling leading to neurite outgrowth.

CD66b ((CGM1); CD67, CGM6, NCA-95) is a glycosylphosphatidylinositol (GPI)-linked protein that is a member of the immunoglobulin superfamily and carcinoembryonic antigen (CEA)-like subfamily. CD66b, expressed on granulocytes, generally is believed to be involved in regulating adhesion and activation of human eosinophils.

CD61 (integrin β3; platelet glycoprotein IIIa; ITGB3) is a cell surface protein composed of an α-chain and a β-chain. A given chain may combine with multiple partners resulting in different integrins. CD61 is found along with the α IIb chain in platelets and is known to participate in cell adhesion and cell-surface mediated signaling.

CD63 (LAMP-3; ME491; MLA1; OMA81H) is a cell surface glycoprotein of the transmembrane 4 superfamily (tetraspanin family). Many of these cell surface receptors have four hydrophobic domains and mediate signal transduction events that play a role in the regulation of cell development, activation, growth and motility. CD63 forms complexes with integrins and may function as a blood platelet activation marker. It generally is believed that the sensitivity and specificity of measuring the upregulation of CD63 alone, or as part of a combination, is not specific enough to serve as a diagnostic marker for the diagnosis of IgE mediated allergy.

CD123 is the 70 kD transmembrane a chain of the cytokine interleukin-3 (IL-3) receptor. Alone, CD123 binds IL-3 with low affinity; when CD123 associates with CDw131 (common β chain), it binds IL-3 with high affinity. CD123 does not transduce intracellular signals upon binding IL-3 and requires the β chain for this function. CD123 is expressed by myeloid precursors, macrophages, dendritic cells, mast cells, basophils, megakaryocytes, and some B cells CD123 induces tyrosine phosphorylation within the cell and promotes proliferation and differentiation within the hematopoietic cell lines.

CD294 (G protein-coupled receptor 44; GPR44; CRTh2; DP2) is an integral membrane protein. This chemoattractant receptor homologous molecule is expressed on T helper type-2 cells. The transmembrane domains of these proteins mediate signals to the interior of the cell by activation of heterotrimeric G proteins that in turn activate various effector proteins that ultimately result a physiologic response.

The term "cytometry" as used herein, refers to a process in which physical and/or chemical characteristics of single cells, or by extension, of other biological or nonbiological particles in roughly the same size or stage, are measured. In flow cytometry, the measurements are made as the cells or particles pass through the measuring apparatus (a flow cytometer) in a fluid stream. A cell sorter, or flow sorter, is a flow cytometer that uses electrical and/or mechanical means to divert and to collect cells (or other small particles) with measured characteristics that fall within a user-selected range of values.

The term "differential label" as used herein, generally refers to a stain, dye, marker, antibody or antibody-dye combination, or intrinsically fluorescent cell-associated molecule, used to characterize or contrast components, small molecules, macromolecules, e.g., proteins, and other structures of a single cell or organism. The term "dye" (also referred to as "fluorochrome" or "fluorophore") as used herein refers to a component of a molecule which causes the molecule to be fluorescent. The component is a functional group in the molecule that absorbs energy of a specific wavelength and re-emits energy at a different (but equally specific) wavelength. The amount and wavelength of the emitted energy depend on both the dye and the chemical environment of the dye. Many dyes are known, including, but not limited to, FITC, R-phycoerythrin (PE), PE-Texas Red Tandem, PE-Cy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyan1, Y77W, S65A, S65C, S65L, S65T, ZsGreen1, ZsYellow1, DsRed2, DsRed monomer, AsRed2, mRFP1, HcRedl, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, Fluor X, BODIDY-FL, TRITC, X-rhodamine, Lissamine Rhodamine B, Texas Red, TruRed, and derivatives thereof.

Flow Cytometry

Flow cytometry is a technique for counting, examining, and sorting microscopic particles suspended in a stream of fluid. It allows simultaneous multi-parametric analysis of the physical and/or chemical characteristics of single cells flowing through an optical and/or electronic detection apparatus.

Flow cytometry utilizes a beam of light (usually laser light) of a single wavelength that is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals found in the particle or attached to the particle may be excited into emitting light at a lower frequency than the light source. This combination of scattered and fluorescent light is picked up by the detectors, and by analyzing fluctuations in brightness at each detector (usually one for each fluorescent emission peak) it then is possible to derive various types of information about the physical and chemical structure of each individual particle. FSC correlates with the cell volume and SSC depends on the inner complexity of the particle (i.e. shape of the nucleus, the amount and type of cytoplasmic granules or the membrane roughness).

FACS

The term "fluorescence-activated cell sorting" (also referred to as "FACS"), as used herein, refers to a method for sorting a heterogeneous mixture of biological cells into one or more containers, one cell at a time, based upon the specific light scattering and fluorescent characteristics of each cell.

Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell. It provides fast, objective and quantitative recording of fluorescent signals from individual cells as well as physical separation of cells of particular interest.

Utilizing FACS, a cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell being in a droplet. Before the stream breaks into droplets the flow passes through a fluorescence measuring station where the fluorescent character of interest of each cell is measured. An electrical charging ring or plane is placed just at the point where the stream breaks into droplets. A charge is placed on the ring based on the prior light scatter and fluorescence intensity measurements, and the opposite charge is trapped on the droplet as it breaks from the stream. The charged droplets then fall through an electrostatic deflection system that diverts droplets into containers based upon their charge. In some systems the charge is applied directly to the stream while a nearby plane or ring is held at ground potential and the droplet breaking off retains charge of the same sign as the stream. The stream is then returned to neutral after the droplet breaks off.

The term "graft" as used herein, refers to any tissue or organ for transplantation. The term "allograft" as used herein, refers to a graft obtained from a donor of the same species as, but with a different genetic make-up from, the recipient, for example, a tissue or organ transplantation between two humans.

The term "graft versus host" as used herein, refers to a systemic autoimmune syndrome resulting from cells of engrafted HCT mounting an immune response against the host. In human recipients of bone marrow, a chronic GvHD syndrome is a major clinical problem, leading to fibrosis, pathology and autoantibodies. The syndrome occurs even in recipients of autologous marrow, although in a milder form. See, e.g., Kennedy, Autologous graft versus host disease. Med. Oncol. 12: 149-15 (1995). Symptoms of chronic GvHD include, but are not limited to, dry eyes or vision changes, dry mouth, white patches inside the mouth, sensitivity to spicy foods, fatigue, muscle weakness, chronic pain, skin rash with raised, discolored areas, skin tightening or thickening, shortness of breath, vaginal dryness and/or weight loss.

The term "hematopoietic stem cell" as used herein, refers to a cell isolated from the blood or from the bone marrow that can renew itself, differentiate to a variety of specialized cells, mobilize out of the bone marrow into the circulating blood, and undergo programmed cell death (apoptosis). In some embodiments of the described invention, hematopoietic stem cells derived from human subjects express at least one type of cell surface marker, including, but not limited to CD34, CD38, HLA-DR, c-kit, CD59, Sca-1, Thy-1, and/or CXCR-4, or a combination thereof.

The term "histocompatibility" as used herein, refers to a state of immunologic similarity (or identity) that permits successful homograft/allograft transplantation.

The term "major histocompatibility complex" (MHC) as used herein, refers to a group of linked loci, collectively termed H-2 complex in the mouse and HLA complex in humans, that codes for cell-surface histocompatibility antigens and is the principal determinant of tissue type and transplant compatibility.

The term "minor histocompatibility complex" as used herein, refers to genes outside of MHC that are present on various chromosomes that encode antigens contributing to graft rejection.

The term "H-Y antigen" as used herein, refers to an antigenic factor, dependent on the Y chromosome, responsible for the differentiation of the human embryo into the male phenotpe by inducing the initially bipotential embryonic gonad to develop into a testis; in the absence of this antigen, the indifferent gonad develops into an ovary. There are at least two loci involved, an autosomal gene that generates the antigen (MIM*543170) and one that makes the receptor (MIM*143150).

The term "human leukocyte antigen (HLA)-DR" as used herein, refers to a major histocompatibility complex (MHC) class II cell surface receptor. HLA-DR commonly is found on antigen-presenting cells such as macrophages, B-cells, and dendritic cells. This cell surface molecule is a $\alpha\beta$ heterodimer with each subunit containing 2 extracellular domains: a membrane spanning domain and a cytoplasmic tail. Both the $\alpha$ and $\beta$ chains are anchored in the membrane. The complex of HLA-DR and its ligand (a peptide of at least 9 amino acids) constitutes a ligand for the TCR.

The term "integrins" as used herein, refers to receptors that mediate attachment between a cell and the tissues surrounding it and are involved in cell-cell and cell-matrix interactions. In mammals, 18 $\alpha$ and 8 $\beta$ subunits have been characterized. Both $\alpha$ and $\beta$ subunits contain two separate tails, both of which penetrate the plasma membrane and possess small cytoplasmic domains.

Integrin αM (ITGAM; CD11b); macrophage-1 antigen (Mac-1); complement receptor 3 (CR3)) is a protein subunit of the heterodimeric integrin αMβ2 molecule. The second chain of αMβ2 is the common integrin β2 subunit (CD18). αMβ2 is expressed on the surface of many leukocytes including monocytes, granulocytes, macrophages and natural killer cells. It generally is believed that αMβ2 mediates inflammation by regulating leukocyte adhesion and migration. Further, αMβ2 is thought to have a role in phagocytosis, cell-mediated cytotoxicity, chemotaxis and cellular activation, as well as being involved in the complement system due to its capacity to bind inactivated complement component 3b (iC3b). The ITGAM subunit of integrin αMβ2 is involved directly in causing the adhesion and spreading of cells, but cannot mediate cellular migration without the presence of the β2 (CD18) subunit.

The term "labeling" as used herein, refers to a process of distinguishing a compound, structure, protein, peptide, antibody, cell or cell component by introducing a traceable constituent. Common traceable constituents include, but are not limited to, a fluorescent antibody, a fluorophore, a dye or a fluorescent dye, a stain or a fluorescent stain, a marker, a fluorescent marker, a chemical stain, a differential stain, a differential label, and a radioisotope.

The term "lymphocyte" refers to a white blood cell formed in lymphatic tissue throughout the body and in normal adults making up about 22-28% of the total number of leukocytes in the circulating blood. Lymphocytes are divided into two principal groups, termed B lymphocytes and T lymphocytes, based on their surface molecules and function.

Lymphocyte activation refers to stimulation of lymphocytes by specific antigens, nonspecific mitogens, or allogeneic cells resulting in synthesis of RNA, protein and DNA and production of lymphokines; it is followed by proliferation and differentiation of various effector and memory cells. The soluble product of an activated B lymphocyte is immunoglobulins (antibodies). The soluble product of an activated T lymphocyte is lymphokines.

The term "mitigate" as used herein, refers to a process of making less severe, serious, or painful.

The terms "peripheral blood mononuclear cells" or "PBMCs" are used interchangeably herein to refer to blood cells having a single round nucleus such as, for example, a lymphocyte or a monocyte. PBMCs are a critical component in the immune system's responses to infections.

The term "stain" as used herein refers to a composition of a dye(s) or pigment(s) used to make a structure, a material, a cell, a cell component, a membrane, a granule, a nucleus, a cell surface receptor, a peptide, a microorganism, a nucleic acid, a protein or a tissue differentiable.

The phrase "subject in need thereof" as used herein refers to a patient that (i) will be administered at least one allograft, (ii) is receiving at least one allograft; or (iii) has received at least one allograft, and is at risk for GvHD, unless the context and usage of the phrase indicates otherwise.

The term "symptom" as used herein refers to a sign or an indication of disorder or disease, especially when experienced by an individual as a change from normal function, sensation, or appearance.

The T Cell Compartment Comprises Distinct T Cell Subsets:

The term "T lymphocyte" or "T cell" generally refers to a thymocyte derived lymphocyte of immunologic importance that is long lived and is responsible for cell mediated immunity. Cellular immunity, the domain of T lymphocytes, is responsible for many immune reactions and is a major element in many autoimmune reactions. T cells are known to directly kill target cells, to provide "help" for such killers, to activate other immune system cells (e.g., macrophages), to help B cells make an antibody response, to down modulate the activities of various immune system cells, and to secrete cytokines, chemokines, and other mediators.

The type 1 and type 2 helper classes are defined by their cytokine secretion profiles. T-helper 1 (Th1) cells, which are implicated in the stimulation of inflammation, produce IFN-gamma, GM-CSF, TNF-beta, and TNFα. TNF and IFN-gamma signals synergize in inducing an activated state in the macrophage, and lead to increased expression of adhesion and homing molecules in the vascular endothelium, which recruit additional blood-born leukocytes to the site of inflammation. (Paul, Fundamentals of Immunol. p. 397). T helper 2 (Th-2) cells produce IL-4, IL-5, IL-10, and IL-13, and provide help for B cells in their activation and differentiation leading to the humoral immune response. (de Waal Malefyt, Immunity 31: 700-702 (2009)).

Regulatory T cells, either natural, induced, or Tr1 cells, produce IL-10 and TGFβ, suppress the activation of effector T cells, and provide a counter-balance against uncontrolled and harmful T cell responses. Id. Th9 cells may provide additional help for mast cells through the production of IL-9. Id. Th17, an additional T cell subset, produces IL-17A, 17-17F, IL-22 and CCL20, which act on stromal and epithelial cells to induce a number of secondary effector molecules, such as G-CSF, which stimulates the production and mobilization of neutrophils, acute phase proteins, chemokines, and antimicrobial peptides. Id.

Naive T cells can differentiate into any of the distinct T cell subsets when activated in the presence of appropriate signals and cytokines. The induction of a maturation process in dendritic cells is a crucial step for efficient priming of naive T cells. There is an extensive cross-regulation between subsets to ensure that the appropriate T cell subset is activated. Id.

The term "transplantation" as used herein, refers to implanting in one part cells, a tissue or organ taken from another part or another individual.

The described invention provides methods useful in warning of onset or recurrence of chronic graft versus host disease (cGvHD) in a patient following a hematopoietic cell transplantation therapy with a hematopoietic cell allograft.

According to one aspect, the described invention provides a method for warning of onset of chronic graft versus host disease (cGvHD) prior to appearance of symptoms of cGvHD in a patient following a hematopoietic cell transplantation therapy with a hematopoietic cell allograft, comprising: (a) isolating peripheral blood mononuclear cells (PBMCs) from the patient at a time after the hematopoietic cell transplantation therapy; (b) analyzing the isolated PBMCs, and specifically detecting a first biomarker expressed by circulating cells of the patient that reacts with a second biomarker expressed by genetically distinct cells, wherein the detecting of the cells that express the first biomarker indicates likely imminent onset of cGVHD in the patient; and (c) initiating immune therapy to mitigate symptoms of cGvHD resulting from the transplant.

According to another aspect, the described invention provides a method for warning of recurrence of chronic graft versus host disease (cGvHD) prior to appearance of symptoms of cGvHD in a patient who, following a hematopoietic cell transplantation therapy with a hematopoietic cell allograft, developed and was treated for cGvHD, which is in remission, comprising: (a) isolating peripheral blood mononuclear cells (PBMCs) from the patient at a time after the hematopoietic cell transplantation therapy; (b) analyzing the isolated PBMCs, and specifically detecting a first biomarker expressed by circulating cells of the patient that reacts with a second biomarker expressed by genetically distinct cells, wherein the detecting of the cells that express the first biomarker indicates likely imminent onset of cGvHD in the patient; and (c) initiating immune therapy to treat the recurrence of the cGvHD resulting from the transplant.

Methods for isolating PBMCs are well-known in the art. Those skilled in the art appreciate that there are many established protocols for isolating PBMCs from peripheral blood. Peripheral blood may be drawn conveniently via venipuncture. Isolation of PBMCs may include, but are not limited to, cell elutriation and density-gradient separation protocols. Exemplary density-gradient separation protocols employ, for example, Ficoll®. Briefly, blood samples may be collected in sodium heparin tubes (BD Biosciences, San Jose, Calif., Catalog No. 367874 or equivalent). Blood may be transferred to 50 mL conical tubes containing 15 mL of Ficoll®-Paque PLUS (GE Healthcare, Waukesha, Wis., Catalog No. 17-1440-03) and centrifuged at 800 rcf (1,900-2,000 rpm) for 20 minutes with centrifuge break off. After centrifugation, the buffy coat layer (containing PBMCs) may be removed and transferred to a new 50 mL conical tube. Phosphate-buffered saline (PBS) without calcium and magnesium (Gibco, Life Technologies, Carlsbad, Calif., Catalog No. 10010-023 or equivalent) may be added to the buffy coat layer so that the total volume in the conical tube is equal to 50 mL. The buffy coat layer in PBS may be centrifuged at 250 rcf (1,200 rpm) for 10 minutes with centrifuge break applied. After centrifugation, the PBS may be aspirated and the PBMC pellet may be resuspended in 48 mL of PBS. PBMCs resuspended in PBS may be centrifuged at 250 rcf (1,200 rpm) for 10 minutes with centrifuge break applied. PBS may be aspirated and PBMC pellet resuspended in 12.5% Human Serum Albumin (HSA) (Gemini Bio-Products, West Sacramento, Calif., Catalog No. 800-120 or equivalent) in RPMI medium (Sigma-Aldrich, St. Louis, Mo., Catalog No. R7388 or equivalent).

It is understood that PBMCs may be analyzed after isolation or cryopreserved for subsequent analysis. Those skilled in the art appreciate that there are many established protocols for cryopreservation of PBMCs. For example, 2× freezing media (10% HSA, Gemini Bio-Products, West Sacramento, Calif., Catalog No. 800-120 or equivalent; 20% Dimethylsulfoxide (DMSO), Sigma-Aldrich, St. Louis, Mo., Catalog No. D2650 or equivalent; RPMI medium, Sigma-Aldrich, St. Louis, Mo., Catalog No. R7388 or equivalent) chilled to 4° C. may be added dropwise to isolated PBMCs at $1 \times 10^7$ viable cells/mL in 12.5% Human Serum Albumin (HSA) (Gemini Bio-Products, West Sacramento, Calif., Catalog No. 800-120 or equivalent) in RPMI medium (Sigma-Aldrich, St. Louis, Mo., Catalog No. R7388 or equivalent) until the freezing media contains a final concentration of 5% HSA, 10% DMSO in RPMI medium. PBMCs in freezing media may be aliquoted into cryovials (Nunc, Thermo Scientific, Waltham, Mass., Catalog No. 12-565-297 or equivalent) (1 mL/cryovial) and placed on ice. Cryovials containing 1 mL of PBMCs in freezing media may be placed in a pre-cooled freezing container (Nalgene, Thermo Scientific, Waltham, Mass., Catalog No. 15-350-50 or equivalent) filled with 70% ethanol (Sigma-Aldrich, St. Louis, Mo., Catalog No. 02877 or equivalent). The freezing container may be placed at −80° C. for 24 hours before cryovials may be transferred to liquid nitrogen.

The described invention provides a method for warning of onset or recurrence of cGvHD by detecting a first biomarker expressed by circulating cells of the patient that reacts with a second biomarker expressed by genetically distinct cells. Possible sources of biomarkers include tissue biopsy and body fluids. Body fluids include, but are not limited to, whole blood, plasma, serum, lymphatic fluid and the like. Possible biomarkers include, but are not limited to, peptides, proteins, glycoproteins, polysaccharides, nucleic acids, antibodies, genes, metabolites, and the like. Exemplary protein biomarkers include, but are not limited to, transforming growth factor beta 1 (TGF-β1), tumor necrosis factor (TNF), interferon gamma (IFN-γ) and B cell activating factor (BAFF). Exemplary nucleic acid biomarkers include, but are not limited to, MHC class I chain-related protein A (MICA)-129 genotype and negative regulator of T cell costimulation CTLA-4+49 A/G*GG genotype.

According to one embodiment, the circulating cells expressing the first biomarker are B lymphocytes with receptors that detect the first biomarker. According to another embodiment, the circulating cells are derived from the hematopoietic cell allograft. According to another embodiment, the receptors are antibodies.

According to one embodiment, the first biomarker is an antibody expressed by cells contained in the hematopoietic cell allograft. According to another embodiment, the cells expressing the first biomarker are B lymphocytes. According to another embodiment, the phenotype of the B lymphocytes is $CD19^+$.

According to one embodiment, the antibody reacts with a second biomarker expressed by the patient's cells. According to another embodiment, the second biomarker is a Y-chromosome encoded H-Y antigen. According to another embodiment, the H-Y antigen is DBY-2.

According to another embodiment, the recipient patient is male, the recipient's cells express the second biomarker, and the second biomarker is the Y-chromosome encoded H-Y antigen, the donor is female, the donor's cells express the first biomarker, and the first biomarker is an antibody, which binds to the second biomarker, which is the H-Y antigen expressed by the patient's cells, wherein the recipient patient and donor are genetically distinct. According to another embodiment, the donor's cells that express the first biomarker are B lymphocytes. According to another embodiment, the phenotype of the B lymphocytes is $CD19^+$.

According to one embodiment, the detecting of the first biomarker expressed by circulating cells of the patient precedes development of circulating antibodies to a donor cell antigen in the patient.

Detection of biomarkers may be accomplished by techniques known in the art, such as, without limitation, enzyme-linked immunosorbent assay (ELISA), Western blot, polymerase chain reaction (PCR), reverse transcription-polymerase chain reaction (RT-PCR), flow cytometry, and the like.

According to one embodiment, the described invention provides the use of flow cytometry to analyze isolated PBMCs. Flow cytometry is a technique for counting and examining small particles such as cells by suspending them in a stream of fluid and passing them by an electronic detection apparatus. Flow cytometry allows simultaneous multiparametric analysis of the physical and/or chemical characteristics of each individual particle or cell. Measurable physical and/or chemical characteristics include, but are not limited to, cell pigments (e.g., chlorophyll and phycoerythrin), total DNA content, total RNA content, DNA copy number variation, chromosome analysis and sorting, protein expression, localization and modification (e.g., phosphorylation), cell surface antigens (e.g., cluster of differentiation (CD) markers), intracellular antigens, nuclear antigens, enzymatic activity, apoptosis, cell viability, cell adherence (e.g., pathogen-host interaction) and the like.

Briefly, a beam of light (e.g., laser light) of a single wavelength is directed onto a hydrodynamically-focused stream of fluid. A number of detectors are aimed at the point where the stream passes through the light beam; one detector in line with the light beam (i.e., forward scatter), several detectors in perpendicular position (i.e., side scatter) and at least one fluorescence detector. Each suspended cell passing through the light beam scatters the light in some way, and fluorescent molecules (i.e., fluorophores) (e.g., naturally occurring or attached label or dye) may be excited into emitting light at a longer wavelength than the light source. The combination of scattered and fluorescent light is recorded by the detectors. The forward scatter correlates with the cell volume, while the side scatter depends upon the inner complexity of the cell (e.g., shape of the nucleus).

One skilled in the art recognizes that a binding agent may be conjugated to a compound that is useful, for example, in cell separation, therapeutic or diagnostic applications employing flow cytometry. Examples of binding agents include, but are not limited to, antibodies, avidin and streptavidin. By way of non-limiting example, a binding agent may be conjugated to a label. The label may be any entity, the presence of which can be readily detected. The label may include, but is not limited to, a direct label, such as those described in detail in May et al., U.S. Pat. No. 5,656,503. Direct labels are entities which, in their natural state, are readily visible either to the naked eye, or with the aid of an optical filter and/or applied stimulation (e.g., laser light) to promote fluorescence. Non-limiting examples of direct labels include radioactive, chemiluminescent, electroactive (e.g., redox labels) and fluorescent (i.e., fluorophore) compounds. Non-limiting examples of fluorophores include Pacific Blue™, Alexa Fluor® 405, Pacific Orange™, Qdot® 525, Qdot® 565, Qdot® 605, Qdot® 655, Qdot® 705, Qdot® 800, Alexa Fluor® 488, RPE (R-Phycoerythrin), RPE Texas Red®, RPE-Alexa Fluor® 610, TRI-COLOR®, RPE-Alexa Fluor® 700, RPE-Cy® 5.5, RPE-Cy® 7, Alexa Fluor® 647, Alexa Fluor® 700, APC-Alexa Fluor® 750 and the like. A binding agent may also be conjugated to, for example, a direct particulate label, such as a dye, metallic (e.g., gold) and colored latex particle. A binding agent may also be conjugated to, for example, a solid support including, but not limited to, a magnetic bead.

Conjugation of a label to a binding agent may be accomplished by covalent or non-covalent (including hydrophobic) bonding, or by adsorption. Techniques for conjugation are well-known in the art and may be readily adapted for the particular reagents employed.

The data generated by flow cytometers may be plotted in a single dimension to produce a histogram or in two-dimensional or three-dimensional plots. The regions on these plots may be sequentially separated, for example, based on fluorescence intensity, by creating a series of subset extractions termed "gates." One skilled in the art recognizes that specific gating protocols exist for diagnostic and clinical purposes, including, but not limited to, classification of immune system cells. By way of example, and without limitation, one skilled in the art would recognize that it is possible to define a light scattering gate to include only B lymphocytes by placing upper and lower limits on the forward and side scatter distributions.

Flow cytometers may use either light scattering in combination with fluorescence or light scattering only for analysis. Flow cytometers are available from a variety of commercial sources, including BD Biosciences (San Jose, Calif.), EMD Millipore (Billerica, Mass.), Life Technologies (Carlsbad, Calif.), Agilent (Santa Clara, Calif.), Miltenyi Biotec (Cambridge, Mass.) and the like.

It is understood that the described invention contemplates several specialized types of flow cytometry well-known in the art. Non-limiting examples include fluorescence-activated cell sorting (FACS®), magnetic-activated cell sorting (MACS®) and high-dimensional flow cytometry.

FACS provides a method of sorting a heterogeneous mixture of cells into two or more containers, a single cell at a time, based upon the specific light scattering and fluorescent characteristics of each cell. The use of multicolor, multiparameter FACS may employ primary conjugated binding agents (e.g., antibodies) at defined fluorophore-to-protein ratios. For example, the following protocol may be used to perform FACS to detect antigen-specific B lymphocytes. PBMCs may be prepared in RPMI medium containing 4% Fetal Calf Serum (FCS) (Gibco, Life Technologies, Carlsbad, Calif., Catalog No. 26010-074 or equivalent) and labeled for 15-30 minutes at 4° C. with a combination of fluorophore-conjugated monoclonal antibodies (mAbs), such as APC-CD19 mAb (BD Biosciences, San Jose, Calif., Clone HIB19, No. 561742 or equivalent), Pacific Blue™-CD27 mAb (BioLegend, San Diego, Calif., Clone 0323, No. 302821 or equivalent), PerCP Cy5.5-IgM mAb (BD Biosciences, San Jose, Calif., Clone G20-127, No. 561285 or equivalent), FITC-Igλ mAb (BD Biosciences, San Jose, Calif., Clone JDC-12, No. 562053 or equivalent) and PE-Igλ mAb (BD Biosciences, San Jose, Calif., Clone G20-193, No. 562052 or equivalent). A 1:50 dilution for specific antibodies, and 1:200 dilution for IgM and IgG controls may be used. The samples may be analyzed by a FACSAria™ II (BD Biosciences, San Jose, Calif.).

MACS provides a cell separation technique in which cells that express a specific surface antigen may be isolated from a heterogeneous mixture of cells using magnetic particles coated with a binding agent (e.g., antibody) that recognizes the specific surface antigen. For example, in a positive cell selection MACS technique, cells expressing the specific surface antigen bind to the magnetic particles. After incubation with the magnetic particles, the heterogeneous mixture of cells is transferred to a column placed in a magnetic field. The magnetic field captures the magnetic particles (including magnetic particles bound to cells expressing the specific surface antigen) while cells not expressing the specific surface antigen (i.e., not bound to magnetic particles) may be eluted as flow through. For example, positive selection involves isolation of cells (e.g., B lymphocytes) expressing a specific surface antigen (e.g., CD19) from a heterogeneous mixture of cells by binding the cells expressing the specific surface antigen to magnetic particles coated with a binding agent (e.g., antibody) that recognizes the specific surface antigen.

It is understood by those in the art that MACS also provides negative selection of cells. Negative selection, for example, involves the isolation and removal of undesired cells expressing a specific surface antigen from a heterogeneous mixture of cells by binding the cells expressing the specific surface antigen to magnetic particles coated with a binding agent (e.g., antibody) that recognizes the specific surface antigen. A magnetic field captures the magnetic particles (including magnetic particles bound to undesired cells expressing the specific surface antigen) while cells not expressing the specific surface antigen (i.e., not bound to magnetic particles) may be eluted and collected.

One skilled in the art recognizes that various MACS products are commercially available. These products include, but are not limited to, MACS microbeads (Miltenyi Biotec, Cambridge, Mass.), autoMACS® columns (Miltenyi Biotec, Cambridge, Mass.), autoMACS Pro Separator Instrument (Miltenyi Biotec, Cambridge, Mass.), and the like.

High-dimensional flow cytometry provides a method of sorting a heterogeneous mixture of cells into two or more containers, a single cell at a time, using 6-12 fluorescent colors (i.e., fluorophores). For example, the following protocol may be used to perform FACS to detect antigen-specific B lymphocytes. Cryopreserved peripheral blood mononuclear cell (PBMC) samples may be thawed and washed in deficient RPMI media supplemented with 4% FCS. Biotin-coupled antigen (DBY-2 or DBX-2) may be added to the cells and 20 minutes later, a "cocktail" of fluorochrome conjugated monoclonal antibodies detecting CD19, CD21$^-$, CD43, CD5, CD23, IgM and IgG, CD27 and dead cells may be added. Following 20 minute incubation, cells may be spun and washed and incubated for 20 min with fluorochrome-conjugated streptavidin. Data may be collected for $1-5\times10^6$ cells on a LSRII flow cytometer (BDBiosciences.com). The data may be analyzed using FlowJo (TreeStar.com) and further analyzed with Excel and Prism (GraphPad software, Inc).

Most parameters measurable by flow cytometry can also be measured by other techniques well-known in the art. These techniques include, but are not limited to, analytical cytology (e.g., microfluorimetry), standard microscopic-based cytometric analysis, physical sorting (e.g., panning), standard immunohistochemical techniques and the like.

The described invention provides the step of initiating immune therapy to mitigate symptoms or to treat recurrence of the cGvHD resulting from the transplant. Examples of immune therapy include, but are not limited, glucocorticoids, mycophenolate mofetil, sirolimus/rapamycin, 2-deoxycoformycin, tacrolimus, rituximab, thalidomide, hydroxychloroquine, interleukin-2 (IL-2), extracorporeal photopheresis, imatinib, pentostatin, mesenchymal stem cells and the like. Exemplary glucocorticoids include, but are not limited to, betamethasone, budesonide, cortisone, dexamethasone, hydrocortisone, methylprednisolone, prednisolone, prednisone, triamcinolone and the like. Symptoms of cGvHD include, without limitation, dry eyes or vision changes, dry mouth, white patches inside the mouth, and sensitivity to spicy foods, fatigue, muscle weakness and chronic pain, skin rash with raised, discolored areas, as well as skin tightening or thickening, shortness of breadth, vaginal dryness and weight loss.

According to one embodiment, patient samples are collected at least at 90 days following HCT. According to another embodiment, patient samples are collected at least at 95 days following HCT. According to another embodiment, patient samples are collected at least at 100 days following HCT. According to another embodiment, patient samples are collected at least at 100 days following HCT. According to another embodiment, patient samples are collected at least at 105 days following HCT. According to another embodiment, patient samples are collected at least at 110 days following HCT. According to another embodiment, patient samples are collected at least at 115 days following HCT. According to another embodiment, patient samples are collected at least at 120 days following HCT. According to another embodiment, patient samples are collected at least at 125 days following HCT. According to another embodiment, patient samples are collected at least at 130 days following HCT. According to another embodiment, patient samples are collected at least at 135 days following HCT. According to another embodiment, patient samples are collected at least at 140 days following HCT. According to another embodiment, patient samples are collected at least at 145 days following HCT. According to another embodiment, patient samples are collected at least at 150 days following HCT. According to another embodiment, patient samples are collected at least at 155 days following HCT. According to another embodiment, patient samples are collected at least at 160 days following HCT. According to another embodiment, patient samples are collected at least at 165 days following HCT. According to another embodiment, patient samples are collected at least at 170 days following HCT. According to another embodiment, patient samples are collected at least at 175 days following HCT. According to another embodiment, patient samples are collected at least at 180 days following HCT. According to another embodiment, patient samples are collected at least at 185 days following HCT. According to another embodiment, patient samples are collected at least at 190 days following HCT. According to another embodiment, patient samples are collected at least at 195 days following HCT. According to another embodiment, patient samples are collected at least at 200 days following HCT. According to another embodiment, patient samples are collected at least at 205 days following HCT. According to another embodiment, patient samples are collected at least at 210 days following HCT. According to another embodiment, patient samples are collected at least at 215 days following HCT. According to another embodiment, patient samples are collected at least at 220 days following HCT. According to another embodiment, patient samples are collected at least at 225 days following HCT. According to another embodiment, patient samples are collected at least at 230 days following HCT. According to another embodiment, patient samples are collected at least at 235 days following HCT. According to another embodiment, patient samples are collected at least at 240 days following HCT. According to another embodiment, patient samples are collected at least at 245 days following HCT. According to another embodiment, patient samples are collected at least at 250 days following HCT. According to another embodiment, patient samples are collected at least at 265 days following HCT. According to another embodiment, patient samples are collected at least at 270 days following HCT. According to another embodiment, patient samples are collected at least at 275 days following HCT. According to another embodiment, patient samples are collected at least at 280 days following HCT. According to another embodiment, patient samples are collected at least at 285 days following HCT. According to another embodiment, patient samples are collected at least at 290 days following HCT. According to another embodiment, patient samples are collected at least at 295 days following HCT. According to another embodiment, patient samples are collected at least at 300 days following HCT. According to another embodiment, patient samples are collected at least at 305 days following HCT. According to another embodiment, patient samples are collected at least at 310 days following HCT. According to another embodiment, patient samples are collected at least at 315 days following HCT. According to another embodiment, patient samples are collected at least at 320 days following HCT. According to another embodiment, patient samples are collected at least at 325 days following HCT. According to another embodiment, patient samples are collected at least at 330 days following HCT. According to another embodiment, patient samples are collected at least at 335 days following HCT. According to another embodiment, patient samples are collected at least at 340 days following HCT. According to another embodiment, patient samples are collected at least at 345 days following HCT. According to another embodiment, patient samples are collected at least at 350 days following HCT. According to another embodiment, patient samples are collected at least at 355 days following HCT. According to another embodiment, patient samples are collected at least at 360 days following HCT. According to another embodiment, patient samples are collected at least at 365 days following HCT.

According to one embodiment, the time after therapy for detecting the first biomarker expressed by circulating cells of the patient is within 1 year after transplantation. According to another embodiment, the time after therapy for detecting the first biomarker expressed by circulating cells of the patient is within 180 days after transplantation. According to another embodiment, the time after therapy for detecting the first biomarker expressed by circulating cells of the patient is within 155 days after transplantation. According to another embodiment, the time after therapy for detecting the first biomarker expressed by circulating cells of the patient is within 90 days after transplantation.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "an", and "the" include plural references unless the context clearly dictates otherwise. All technical and scientific terms used herein have the same meaning.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

METHODS

Human Subjects

Since Oct. 1, 2005, all allogeneic HCT patients were invited to participate in an ongoing IRB approved research protocol that cryopreserves PBMC and plasma samples collected 3, 6, and 12 months (+/−15%) following F→M HCT in the BMT tissue bank at Stanford Stem Cell Transplantation Laboratory. Because patients' clinic schedules vary, a 15% leeway was allowed for each research sample collection time point. All samples were obtained from patients providing informed consent and the research sample protocol was monitored by the Stanford University School of Medicine Institutional Review Board. All patients suspected of cGVHD development were evaluated in real-time by one of three dedicated Stanford cGVHD clinicians and further reviewed by cGVHD Scoring committee to uniformly apply NIH consensus cGVHD criteria (Filipovich A H, et al. (2005) National Institutes of Health consensus development project on criteria for clinical trials in chronic graft-versus-host disease: I. Diagnosis and staging working group report. Biol Blood Marrow Transplant 11:945-956). For this retrospective study, we identified a consecutive series of 28 male patients with female donors who had enrolled on our research sample protocol with their transplant dates ranging Jan. 17, 2006-May 12, 2010, and who had survived at least one year with research blood samples successfully collected 6 and 12 months following HCT. All patients had undergone transplantation for lymphoid and blood malignancies and are described in Table 1.

Donor Chimerism Analysis

Donor chimerism analyses were performed on whole blood and PBMCs separated into CD3, CD19, populations using Dyna1-coated immunomagnetic beads. Donor engraftment used DNA genotyping of simple sequence-length polymorphic markers that encode short tandem repeats, as described previously (Millan M T, et al. (2002) Mixed chimerism and immunosuppressive drug withdrawal after HLA-mismatched kidney and hematopoietic progenitor transplantation. Transplantation 73:1386-1391).

Detection of Serum Antibodies Reactive with DBY and DBY-2

The ELISA protocol that we use has been published (Miklos D B, et al. Antibody response to DBY minor histocompatibility antigen is induced after allogeneic stem cell transplantation and in healthy female donors. Blood 103:353-359; Miklos D B, et al. (2005) Antibody responses to H-Y minor histocompatibility antigens correlate with chronic graft-versus-host disease and disease remission. Blood 105:2973-2978). Briefly, purified DBY, DBX, DBY-2 (KNDPERLDQQLANLDLNSEK) (SEQ ID NO: 1) and DBX-2 (ENALGLDQQFAGLDLNSSD) (SEQ ID NO: 2) (disparate amino acids are bolded) and HIVp24 (negative control) proteins were coated onto 96-well ELISA plates. The ELISA plates were blocked with 2% nonfat dry milk powder in tris buffered saline-tween 20 (TBST) for 2 hrs before the patient plasma and controls were added. The plates were incubated overnight at 4° C., washed and goat antihuman immunoglobulin G (IgG) conjugated to alkaline phosphatase was added to detect bound IgG antibodies. Finally, a chromogenic alkaline phosphatase substrate was added and the absorbance at 405 and 450 nm determined 30 min later. Data for readings at 450 nm are reported to maintain continuity with previous assays. Values >3 s.d. above the mean for 32 healthy male donor samples were considered positive.

High-Dimensional Flow Cytometry Analysis

Cryopreserved peripheral blood mononuclear cell (PBMC) samples were thawed and washed in deficient RPMI media supplemented with 4% FCS. Greater than 90% viable PBMC were detected after thawing. Biotin-coupled antigen (DBY-2 or DBX-2) was added to the cells and 20 minutes later, a "cocktail" of fluorochrome conjugated monoclonal antibodies detecting CD19, CD21⁻, CD43, CD5, CD23, IgM and IgG, CD27 and dead cells was added. Following 20 minute incubation, cells were spun and washed and incubated for 20 min with fluorochrome-conjugated streptavidin. Data was collected for $1-5\times10^6$ cells on a LSRII flow cytometer (BDBiosciences.com). The data was analyzed using FlowJo (TreeStar.com) and further analyzed with Excel and Prism (GraphPad software, Inc).

Fluorescence Activated Cell Sorting (FACS-Sort)

PBMC were thawed and stained as described above. Antigen specific B cells were sorted into FCS using a custom ARIAII (BDBioSciences.com) instrument. Approximately 70% of the sorted viable cells were recovered.

Culture Conditions

DBY-2 specific CD19+ B cells and CD3+ T cells were separately sorted with FACS and cells were co-cultured (106/ml) in RPMI with 10% fetal calf serum and DBY protein (0.05 µg/ml). IL-2 (50 IU/ml) and BAFF (RNDsystems.com) were tested at 10 ng/ml. Cultures were maintained at 37° C. with 5% $CO_2$ in 5% $O_2$ incubators (Sahaf B, et al. (2008) Culturing of human peripheral blood cells reveals unsuspected lymphocyte responses relevant to HIV disease. Proc Natl Acad Sci USA 105:5111-5116). Harvested supernatant was stored at –80° C. before IgG ELISA assays.

Statistical Analyses

Non-parametric Kruskal-Wallis, Mann Whitney-U tests and Fisher Exact test were used as indicated. The tests were performed in Prism (GraphPad Software, Inc).

Example 1

Retrospective Study Design

This study characterized a series of 28 consecutive female to male hematopoietic cell transplantation (F→M HCT) who consented to research blood sample collection before transplant and had samples cryopreserved 6 and 12 months after hematopoietic cell transplantation (HCT). Blood research samples were tested without knowledge of patient disease status, GVHD development or other clinical characteristics. Patient characteristics are described in Table 1.

Example 2

B Cells Circulating in F→M HCT Patients Express Immunoglobulin (Ig) Receptors Specific for DBY-2, an Immuno-Dominant Epitope in the DBY Protein B cells circulating in F→M HCT patients express Ig receptors specific for DBY-2, an immuno-dominant epitope in the DBY protein. The DBY-2 peptide (KND-PERLDQQLANLDLNSEK) (SEQ ID NO: 1) contains the DBY-2 epitope frequently recognized in allogeneic F→M antibody responses that occur following HCT (Miklos D B, et al. Antibody response to DBY minor histocompatibility antigen is induced after allogeneic stem cell transplantation and in healthy female donors. Blood 103:353-359; Miklos D B, et al. (2005) Antibody responses to H-Y minor histocompatibility antigens correlate with chronic graft-versus-host disease and disease remission. Blood 105:2973-2978). Previous studies showed that 35% of F→M patients develop circulating IgG anti DBY-2 antibodies detectable by ELISA six months to one year following HCT (Miklos D B, et al. Antibody response to DBY minor histocompatibility antigen is induced after allogeneic stem cell transplantation and in healthy female donors. Blood 103:353-359). Extending this work, we used FACS analyses to reveal circulating live B cells expressing Ig receptors that specifically bind DBY-2, defined as those cells whose DBY-2 binding level is above a threshold defined by the Fluorescence Minus One (FMO) control. i.e., a sample stained with all reagents except DBY-2 peptide (FIG. 1). Cells expressing either anti DBY-2 associated with Igκ or Igλ light chains by definition fall within this FMO gate. FIG. 1 shows the gating scheme and data for a representative patient sample.

Figure 3:
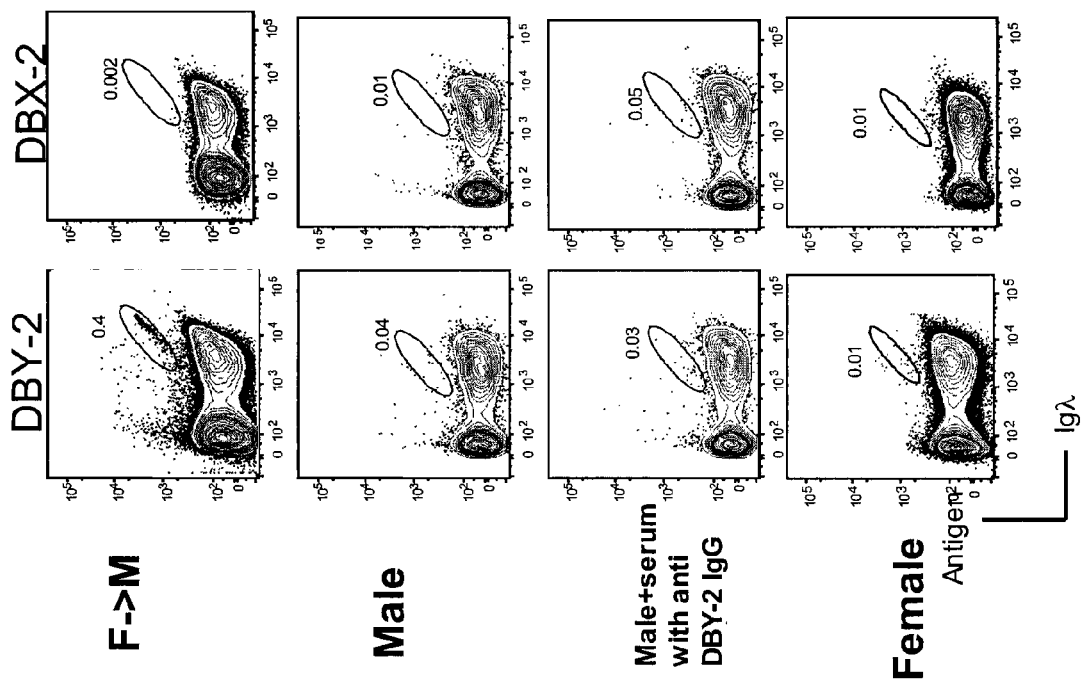
FIG. 3 depicts gated FACS data illustrating DBY-2 binding B cells are detected in some F→M patients after HCT but not in healthy males and female donors. Data for a representative F→M HCT patient collected 180 days post HCT (upper panel) and for health controls (lower 3 panels). Less than 0.1% DBY-2 specific B cells were detected in 15 normal male and 8 female samples. The third row shows no DBY-2 specific B cells were detected following pre-incubation of serum collected from F→M HCT containing high-titer anti-DBY-2 IgG with normal male donor PBMCs and suggests DBY-2 staining observed after F→M HCT is not an indirect IgG mediated binding but rather cell specific IgM dependent binding.
Figure 4:
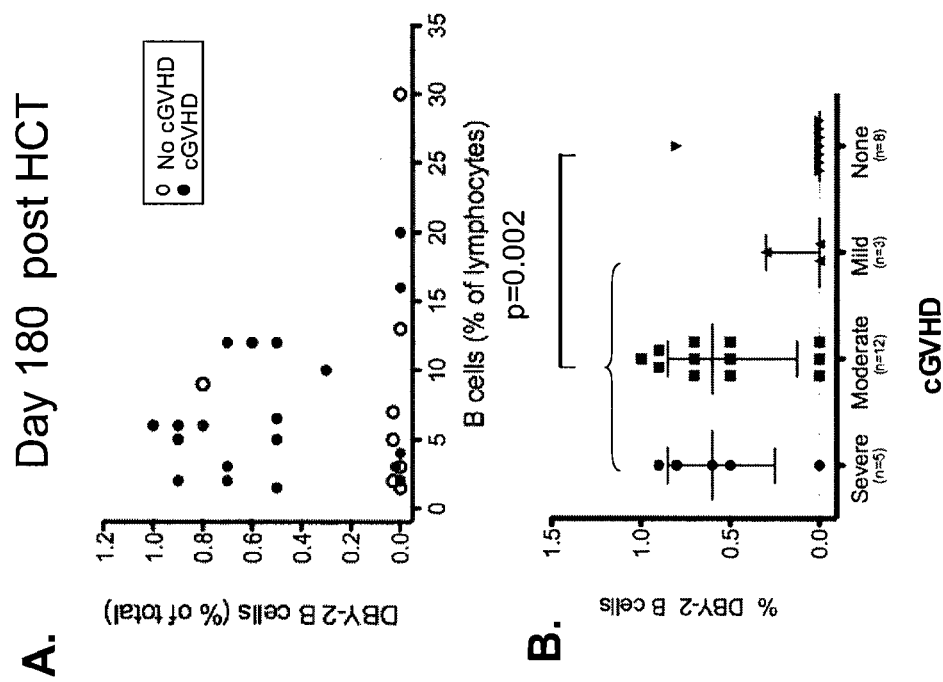
FIG. 4 illustrates anti-DBY-2 B cell frequencies quantified 180 days after 28 F→M HCT. Y-axis in both the upper and lower panels shows the relative frequency of DBY-2 binding B cells in relation to total PBMC lymphocytes shown on the X-axis (above) or in relation to cGVHD severity (below). Upper panel: open circles indicate cGVHD patients; closed circles show similar data for patients who did not develop cGVHD. In the lower panel anti-DBY-2 B cell staining associates with any cGVHD development in comparison to none (p=0.004; Fisher exact test).

DBY-2 binding B cells (FIG. 1, lower left panel) were detected in 16 of 28 (57%) PBMC samples collected 6 months following F→M HCT (FIG. 2). As expected, these DBY-2 B cells were not detected in PBMC from 15 healthy males where H-Y antigens are "self" antigens. DBY-2 B cells were not detected in healthy female HCT donor PBMC samples (FIG. 3). Importantly, DBY-2 specific B cells were not detected following pre-incubation of high-titer anti DBY-2 IgG with normal male donor PBMCs. We conclude the DBY-2 staining B cells observed after F→M HCT does not result from indirect IgG binding but rather cell specific IgM expression. Cognizant that immune reconstitution after myeloablative and nonmyeloablative conditioning may differ, we included a similar number of 15 myeloablative and 13 nonmyeloablative conditioned F→M patients, and their detection of DBY-2 specific B cells did not statistically differ (Table 2). As shown in FIG. 4A, the median absolute number of B cells detected 6 months following allo-HCT was 136/µl and ranged between 18 and 400. The absolute number of CD19⁺ B cells did not statistically differ in relation to conditioning intensity or donor relationship (data not shown). The DBY-2 binding B cells collected from transplant patients' blood are donor derived since both whole blood and CD19+ B cells showed greater than 95% donor origin as measured by short tandem repeat (STR) 3 months following transplantation.

TABLE 2

Univariable Analyses of DBY-2 B cells and DBY-2 IgG Development

|  | DBY-2 B cells Day 180 | aDBY-2 IgG+ within 1 y post HCT |
|---|---|---|
|  | 16/28 (57%) | 14/28 (50%) |
| Conditioning |  |  |
| Myeloablative | 8/13 (62%) | 6/13 (43%) |
| Nonmyeloablative | 7/15 (47%) | 9/15 (60%) ns‡ |
| Donor |  |  |
| Related | 11/16 (67%) | 9/16 (56%) |
| Unrelated | 6/12 (42%) | 5/12 (42%) ns‡ |
| cGVHD |  |  |
| None | 1/8 (12.5%) | 2/8 (25%) |
| Mild | 1/3 (33%) | 0/3 (0) |
| Moderate | 9/12 (75%) | 8/12 (67%) |
| Severe | 5/5 (100%) p = 0.004 | 4/5 (80%)* p = 0.01 |

*Comparing cGVHD (Severe, Moderate, Mild) against none
‡ns = not significant

The DBY-2 binding B cells in the transplant patients generally expressed both Igκ and Igλ DBY-2 receptors. In the lower right panel in FIG. 1, the Igκ expressing anti DBY-2 cells are bounded by the square insert on the left side of the figure and the Igλ expressing anti DBY-2 cells are bounded by the oval on the right. The amount of DBY-2 bound to cells with Igλ-containing receptors tends to be proportional to the level of receptor expression on the cells, resulting in the "diagonal" distribution for DBY-2 binding cells that is visible when DBY2 binding is plotted against Igλ expression (FIG. 1, lower right panel). The "tightness" of this diagonal suggests that the Igλ-containing receptors for DBY-2 are expressed at varied levels but that the binding avidity of the receptors is fairly similar. This diagonal pattern is expected for monoclonal antibodies or for a group of cells in which single or closely related Ig sequences are responsible for the antigen binding. Diagonal patterns were not observed with Igκ DBY-2 binding cells in any of the subjects tested.

Example 3

Figure 2A:
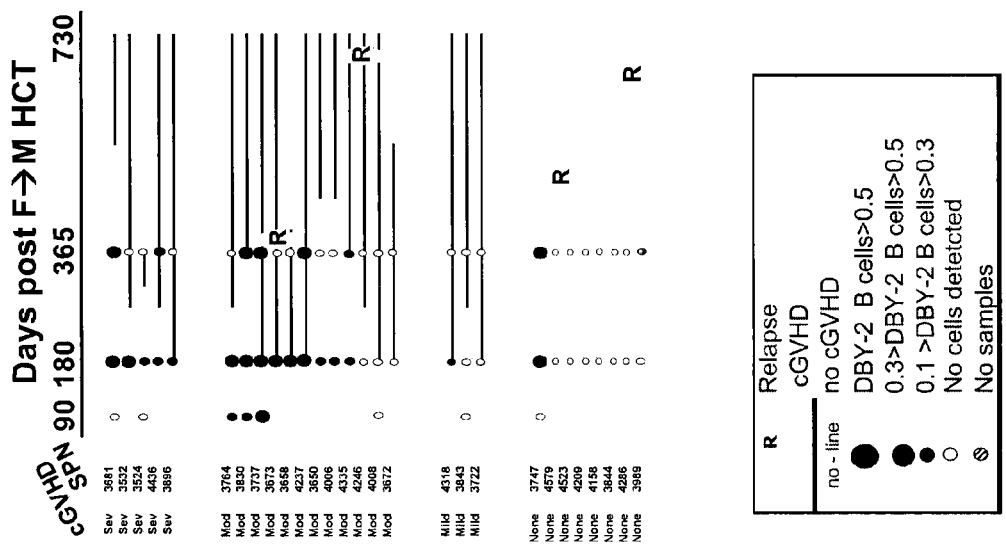
FIG. 2A schematically illustrates the temporal development of anti-DBY-2 B cells and cGVHD for 28 F→M patients with clinical follow-up through 730 days (X-axis). Filled circles indicate the presence of DBY-2 specific B cells; circle size reflects the percentage of these B cells among PBMC lymphocytes. Open circles indicate that anti-DBY-2 B cell frequencies were below detectability (<0.1%) of PBMC lymphocytes. Solid lines indicate cGVHD onset and duration. "R" marks time of hematologic malignancy relapse.

Presence of B Cells with Receptors Specific for DBY-2 at Day 180 Precedes Development of cGVHD in the Majority of F→M Transplant Patients FIG. 2A schematically presents each patient's temporal development of cGVHD in relation to their 6 and 12 month DBY-2 B cell measurements. The detection of DBY-2 B cells is highly associated with cGVHD (p=0.004; FIG. 2A). Considering the 16 patients in whom DBY-2 binding B cells were detected 180 days following F→M HCT, 15 ultimately developed cGVHD. For 6 patients, the "day 180" clinic visit was also their cGVHD diagnosis date (ranging 155-182 days following HCT). The 9 others with DBY-2 B cells detected were diagnosed with cGVHD at later clinic visits. Interestingly, the absolute and relative number of DBY-2 specific B cells was significantly higher 6 months following HCT in patients who developed moderate or severe cGVHD compared to those with mild cGVHD or none (p=0.02; FIG. 4B). In these 28 F→M HCT, none had cGVHD diagnosed before their 6 months sample collection. It may be important that our earliest diagnosis of cGVHD was 155 days after HCT, since cGVHD can sometimes develop as early as 90 days following HCT, but our limited patients sample did not happen to include such early cGVHD. While samples collected at 90 days following HCT were available for only 8 patients, we have included this limited day 90 data in FIG. 2A because 3/9 had detectable DBY-2 B cells and suggests that follow-up studies should include samples collected as early as 90 days following HCT.

Example 4

Figure 2B:
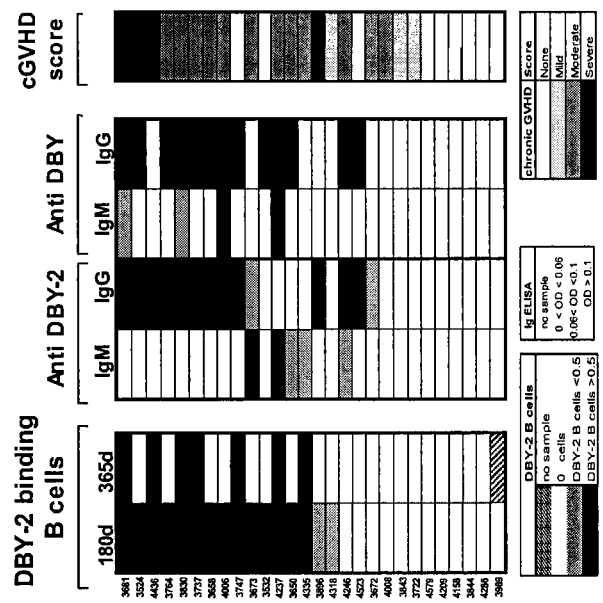
FIG. 2B schematically illustrates the frequency of DBY-2 B cells detected at 180 and 365 days are related to Ig development against DBY-2 peptide epitope, full-length DBY protein, and cGVHD development. cGVHD patients were ranked by frequency of DBY-2 B cells detected 180 days following transplant and secondarily by presence of IgG anti-DBY-2 in serum. Other columns include the unique Stanford Patient Number (SPN), each patient's NIH cGVHD score, the maximum IgM and IgG anti-DBY or anti-DBY-2 levels measured by ELISA within 1 year post HCT. The Figure legends indicate the relative intensity of each value.

The Detection of DBY-2 Specific B Cells Precedes the Development of Circulating Anti-DBY Antibodies As expected, the majority (11 of 14) of the F→M transplant patients who had anti DBY-2 IgG develop within 1 year post HCT also had DBY-2 specific B cells detected 180 days following HCT (FIG. 2B). Interestingly, the number of patients who had anti DBY-2 B cells detected from PBMC collected one year post transplant was than lower than the day 180 frequency (FIG. 2B). This may be due to the migration of cells from blood into lymphoid organs. Additionally, the cells may have been eliminated by treatment for cGVHD.

Example 5

The Detection of Anti-DBY-2 IgG Within One Year Post F→M HCT Associates with cGVHD Development Circulating anti DBY-2 IgG was detected in plasma collected from 14 of 28 (50%) patients within one year of transplant. As we previously reported for allogeneic IgG developing against any of five full-length H—Y antigens (20) the detection of anti DBY-2 IgG associated with the development of cGVHD (p=0.002) and did not associate with patient's primary disease, conditioning regimen, or donor relationship (Table 2). None of these 28 F→M HCT patients had DBY-2 IgG detected in their 6 month samples when already 16 of 28 (57%) had detectable DBY-2 B cells. Our demonstration that these DBY-2 specific B cells appear prior to development of both their corresponding IgG and cGVHD suggests that detection of anti DBY-2 B cells may predict cGVHD with clinical utility.

Example 6

Figure 5:
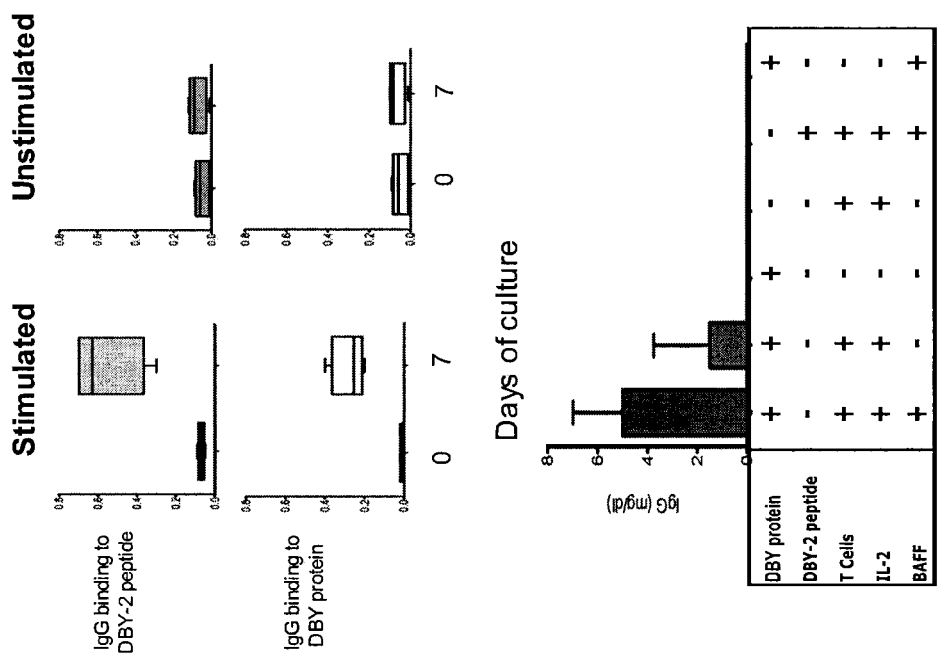
FIG. 5 illustrates that DBY-2 binding B cells secret IgG in presence of T cells and DBY-antigen. FACS sorted DBY-2 binding B cells are incubated in the absence (upper left panels) or in the presence (Upper right panels) of autologous T cells, IL-2, DBY-protein and BAFF. Relative IgG antibody levels for DBY-2 and DBY proteins are shown after 7 days of incubation. Secreted IgG levels were determined in presence of the reagents as depicted below X-axis for n=9 first column, n=4 for second column, n=2 for third and subsequent conditions.

IgG that Binds DBY Protein and DBY-2 Peptide is Secreted Following Ex Vivo Stimulation of FACS-Sorted Anti-DBY-2 Specific B Cells FACS sorted DBY-2 binding B cells cultured with DBY protein plus IL-2, B cell activating factor (BAFF) and autologous T cells for seven days secreted ELISA-detectable IgG that specifically detected DBY-2 and the full-length DBY protein (FIG. 5, upper panel). Both the intact DBY protein and autologous T cells were required for this stimulation since virtually no detectable antibody was produced if either was omitted from the culture. In contrast, BAFF was helpful but not necessary for antibody production (FIG. 5, lower panel). The requirement for T cells and the full-length protein antigen suggests that this anti DBY-2 response is T-dependent.

Example 7

FACS Phenotype of the DBY-2 Binding B Cells in F→M Patients

Figure 6:
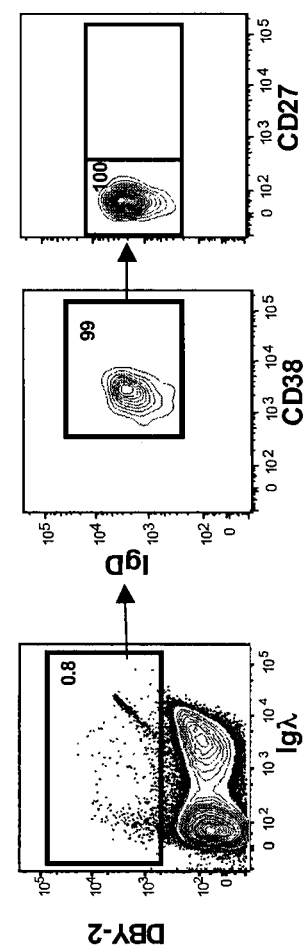
FIG. 6 depicts gated FACS data illustrating a phenotype of the DBY-2 binding B cells. Singlet, live, lymphocyte, B cells are gated for the presence of DBY-2 binding and Igλ. These cells are further shown to be IgD$^+$, CD38$^+$ and CD27$^-$.

The median frequency of DBY-2 binding B cells in the F→M patients is 0.7% (0.3-1.0%) of CD-19 B cells (FIG. 4A). This relatively high frequency is in the range (>0.1%) frequently observed for antigen reactive cells in immunized hosts. Nevertheless, the phenotype of these cells corresponds to the commonly accepted phenotype for naïve B cells in man, i.e., $CD19^+IgM^+IgD^+CD27^-CD38^+CD5^-$ (FIG. 6). None of the DBY-2 binding B cells in the F→M HCT patients express CD27, which is typically expressed on memory B cells. However, occasional blood samples drawn when GVHD is present contained cells expressing the typical phenotype for isotype-switched plasmablasts $(CD19^+IgM^+IgD^+Ig\lambda^+CD27^+CD38^+CD5^-)$.

TABLE 3

Antibody Characteristics for the
Marker Combinations in Hi-D FACS

| Antigen | Fluorochrome | Source |
|---|---|---|
| CD19 | APC | BD Biosciences |
| CD56 | Cy5PE | BioLegend |
| CD14 | Cy5PE | BioLegend |
| CD3 | Cy5PE | BioLegend |
| IgD | Alexa 700 | BioLegend, as purified anitbody |
| IgM | PecP CY5.5 | BD Biosciences |
| CD38 | Cy7PE/or Qdot655 | BD Biosciences |
| CD27 | Pacific-Blue | BioLegend |
| Ig Lambda | FITC | BD Biosciences |
| Ig Kappa | PE | BD Biosciences |

DISCUSSION

This study reports a FACS method pairing antigen specific staining with paired B cell receptor detection using lambda/kappa light chain detection to identify a high frequency alloreactive donor B cell binding DBY-2 that develops following allogeneic F→M HCT and is not detected in normal male or female donors. These cells were detected in fifteen of sixteen F→M HCT recipients who developed chronic graft versus host disease (cGVHD). In contrast, they were only detected in one of eight patients who did not develop cGVHD. Thus we conclude that the presence of B cells with receptors that recognize the DBY-2 is positively associated with development of cGVHD ($p<0.004$, Fisher Exact Test).

Previous studies have shown that H—Y antibody develop following F→M HCT in association with cGVHD (Miklos D B, et al. (2005) Antibody responses to H-Y minor histocompatibility antigens correlate with chronic graft-versus-host disease and disease remission. Blood 105:2973-2978), and here we show immune dominant peptide epitope DBY-2 was similarly recognized by IgG in 50% of these 28 F→M HCT patients and associated with cGVHD ($p=0.002$). However, these H-Y IgG antibodies are rarely detected prior to the onset of GVHD and thus are unlikely to have cGVHD predictive value. In contrast, this study identifies B cells that express IgM and IgG receptors specific for DBY-2 and show that these alloantigen binding B cells often precede the onset of cGVHD. Thus, their presence in a patient may warrant pre-emptive cGVHD therapy.

The role that DBY-2 binding B cells play in the cGVHD disease process is unclear. They may simply be bystanders that are induced by mechanisms that activate T cells that may actually mediate cGVHD. However, our observation that they commonly preceded cGVHD developments suggests that they may play an early pathogenic role. In fact, as recent findings with mouse GVHD models suggest, they may play a role in antigen presentation (23) necessary for stimulation of pathogenic T cell clonal expansion and/or induction of inflammatory cytokine production and alloreactive antibody production (Young J S, et al (2012) Donor B cells in transplants augment clonal expansion and survival of pathogenic CD4+ T cells that mediate autoimmune-like chronic graft-versus-host disease. J Immunol 189:222-233; Srinivasan M, et al. (2011) Donor B-cell alloantibody deposition and germinal center formation are required for the development of murine chronic GVHD and bronchiolitis obliterans. Blood 119:1570-1580).

The DBY-specific B cells are found in F→M transplant patients where, by virtue of the sex mismatch between donor and host, the donor B cells are extensively exposed to the host DBY protein and its component DBY-2 peptide. Consistent with this argument, the DBY-2 binding B cells in the F→M patients are present at the relatively high frequencies common for antigen reactive cells generated in response to an antigenic stimulus.

Basically, the presence of DBY-2 binding B cells in F→M patients would lead us to believe that they are memory B cells that developed from naïve female donor B cells when they encountered the host DBY-2 antigen. However, the phenotype of these anti DBY-2 B cells corresponds to the commonly accepted phenotype for human naïve or transitional B cells ($CD19^+IgD^+IgM^+CD27^-CD38^+CD5^-$) (Kuzmina Z, et al. (2011) Significant differences in B-cell subpopulations characterize patients with chronic graft-versus-host disease-associated dysgammaglobulinemia. Blood 117:2265-2274; Sarantopoulos S, et al. (2007) High levels of B-cell activating factor in patients with active chronic graft-versus-host disease. Clin Cancer Res 13:6107-6114; Sarantopoulos S, et al. (2011) Recovery of B-cell homeostasis after rituximab in chronic graft-versus-host disease. Blood 117:2275-2283; Sarantopoulos S, et al. (2009) Altered B-cell homeostasis and excess BAFF in human chronic graft-versushost disease. Blood 113:3865-74; Young J S, et al (2012) Donor B cells in transplants augment clonal expansion and survival of pathogenic CD4+ T cells that mediate autoimmune-like chronic graft-versus-host disease. J Immunol 189:222-233) that have recently emerged from bone marrow and are on their way to lymphoid organs. Although these B cells may ultimately give rise to the plasma cells that produce the IgG anti DBY-2 found in circulation later in the disease, their current phenotype belies this fate. Future studies may help to resolve this paradox.

In summary, we show here for the first time that F→M HCT patients commonly develop donor B cells with Ig receptors that recognize host male antigens. These B cells, which develop prior to, or concurrent with the onset of cGVHD, precede the onset of antibodies production to male H-Y antigens. These findings may provide a mechanistic explanation for the moderate efficacy of in vivo B cell depletion in treating cGVHD, and further suggests that more focused B cell targeting, e.g., with DBY-2 in F→M HCT, might be more effective cGVHD therapy. In addition, the prospective monitoring of anti DBY-2 B cells may direct a more effective schedule for alloreactive B cell depletion therapy towards a goal of cGVHD prevention. Finally, DBY-2 B cell monitoring will help elucidate whether current in vivo B cell depletion therapy for cGVHD effectively depletes these alloreactive B cells or if they persist and proliferate when cGVHD recurs.

What is claimed is:

1. A method for treating chronic graft versus host disease (cGvHD) prior to appearance of symptoms of cGvHD in a patient following a hematopoietic cell transplantation therapy with a hematopoietic cell allograft comprising hematopoietic cells from a genetically distinct donor, comprising:
   (a) isolating peripheral blood mononuclear cells (PBMCs) comprising the genetically distinct donor cells from the patient at a time after the therapy;
   (b) detecting an alloreactive donor B cell population in the isolated PBMCs by detecting reactivity in vitro of a first biomarker presented on the alloreactive donor B cells with a second biomarker expressed by genetically distinct cells of the patient, the second biomarker having a differential label;
   (c) initiating immune therapy to mitigate appearance of symptoms of cGvHD resulting from the hematopoietic cell transplant if alloreactive donor B cells are detected by step (b).

2. The method according to claim 1, wherein the first biomarker is an antibody, the hematopoietic cell allograft contains cells that express the antibody, and the antibody reacts with the second biomarker expressed by the patient's cells.

3. The method according to claim 2, wherein the second biomarker is a Y-chromosome encoded H-Y antigen.

4. The method according to claim 3, wherein the H-Y antigen is the peptide sequence according to SEQ ID NO: 1.

5. The method according to claim 3, wherein the recipient patient is male, the recipient's cells express the second biomarker, and the second biomarker is the Y-chromosome encoded H-Y antigen, the donor is female, the donor's cells express the first biomarker, and the first biomarker is an antibody, which binds to the second biomarker, which is the H-Y antigen expressed by the patient's cells, wherein the recipient patient and donor are genetically distinct.

6. The method according to claim 5, wherein phenotype of the B lymphocytes is CD19$^+$.

7. The method according to claim 1, wherein the time after therapy for detecting the first biomarker presented on circulating cells of the patient is within 1 year after transplantation.

8. The method according to claim 1, wherein the time after therapy for detecting the first biomarker presented on circulating cells of the patient is within 180 days after transplantation.

9. The method according to claim 1, wherein the time after therapy for detecting the first biomarker presented on circulating cells of the patient is within 155 days after transplantation.

10. The method according to claim 1, wherein time after therapy for detecting of the first biomarker presented on circulating cells of the patient is within 90 days after transplantation.

11. The method according to claim 1, wherein detecting of the first biomarker presented on circulating cells of the patient precedes development of circulating antibodies to a donor cell antigen in the patient.

12. The method according to claim 1, wherein identifying step (b) is performed using flow cytometry.

* * * * *

SEQUENCE LISTING

<160> NUMBER OF SEQ ID NOS: 2

<210> SEQ ID NO 1
<211> LENGTH: 20

```
<212> TYPE: PRT
<213> ORGANISM: Homo sapiens

<400> SEQUENCE: 1

Lys Asn Asp Pro Glu Arg Leu Asp Gln Gln Leu Ala Asn Leu Asp Leu
1               5                   10                  15

Asn Ser Glu Lys
            20

<210> SEQ ID NO 2
<211> LENGTH: 19
<212> TYPE: PRT
<213> ORGANISM: Homo sapiens

<400> SEQUENCE: 2

Glu Asn Ala Leu Gly Leu Asp Gln Gln Phe Ala Gly Leu Asp Leu Asn
1               5                   10                  15

Ser Ser Asp
```